US009801948B2

(12) United States Patent
Altman et al.

(10) Patent No.: US 9,801,948 B2
(45) Date of Patent: Oct. 31, 2017

(54) ANTIMICROBIAL COMPOSITIONS AND METHODS OF USE THEREOF

(71) Applicant: Yale University, New Haven, CT (US)

(72) Inventors: Sidney Altman, Hamden, CT (US); Alfred Bothwell, Guilford, CT (US); Choukri Mamoum, Farmington, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/343,809

(22) PCT Filed: Sep. 21, 2012

(86) PCT No.: PCT/US2012/056687
§ 371 (c)(1),
(2) Date: Mar. 7, 2014

(87) PCT Pub. No.: WO2013/044116
PCT Pub. Date: Mar. 28, 2013

(65) Prior Publication Data
US 2014/0220086 A1 Aug. 7, 2014

Related U.S. Application Data

(60) Provisional application No. 61/537,326, filed on Sep. 21, 2011, provisional application No. 61/590,062, filed on Jan. 24, 2012.

(51) Int. Cl.
*C07K 16/00* (2006.01)
*A61K 47/48* (2006.01)
*C12Q 1/18* (2006.01)

(52) U.S. Cl.
CPC .. *A61K 47/48246* (2013.01); *A61K 47/48092* (2013.01); *C12Q 1/18* (2013.01)

(58) Field of Classification Search
None
See application file for complete search history.

(56) References Cited

U.S. PATENT DOCUMENTS

| 5,034,506 A | 7/1991 | Summerton |
| 5,142,047 A | 8/1992 | Summerton |
| 5,166,315 A | 11/1992 | Summerton |
| 5,217,866 A | 6/1993 | Summerton |
| 5,506,337 A | 4/1996 | Summerton |
| 5,521,063 A | 5/1996 | Summerton |
| 5,527,675 A | 6/1996 | Coull |
| 5,539,082 A | 7/1996 | Nielsen |
| 5,623,049 A | 4/1997 | Lobberding |
| 5,624,824 A | 4/1997 | Yuan |
| 5,698,685 A | 12/1997 | Summerton |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 5,976,874 A | 11/1999 | Altman |
| 6,610,478 B1 | 8/2003 | Takle |
| 2005/0196862 A1 | 9/2005 | Wooddell |
| 2011/0172107 A1 | 7/2011 | Katz |

FOREIGN PATENT DOCUMENTS

| WO | 9203566 | 3/1992 |
| WO | 9322434 | 11/1993 |
| WO | 9524489 | 9/1995 |
| WO | 9621731 | 7/1996 |
| WO | 2009069935 | 6/2009 |

OTHER PUBLICATIONS

Stewart et al. Org. Chem. 2008, 6, 2242-2255.*
Abes, et al., "Vectorization of morpholino oligomers by the (R-Ahx-R)4 peptide allows efficient splicing correction in the absence of endosomolytic agents", J Control Release, 116:304-13 (2006).
Anonymous, "A research agenda for malaria eradication: drugs", PLoS Med, 8(1):e1000402 (2011).
Armstrong, et al., "An fkbp destabilization domain modulates protein levels in plasmodium falciparum", Nat Methods, 4(12):1007-9 (2007).
Augagneur, et al., "Gene selective mRNA cleavage inhibits the development of Plasmodium falciparum", PNAS, 109(16):6235-40 (2012).
Bennett, et al., "Protein delivery using VP22", Nat. Biotechnol. 20:20 (2002).
Braasch, et al., "Locked nucleic acid (LNA): fine-tuning the recognition of DNA and RNA", Chem. Biol., 8(1):1-7 (2001).
Choi, et al., "Cell-permeable Foxp3 protein alleviates autoimmune disease associated with inflammatory bowel disease and allergic airway inflammation.", PNAS, 107:18575-80 (2010).
Crowther, et al., "Identification of attractive drug targets in neglected-disease pathogens using an in silico approach", PLoS Negl Trop Dis, 4(8):e804 (2010).

(Continued)

*Primary Examiner* — Ja'Na Hines
*Assistant Examiner* — Khatol Shahnan Shah
(74) *Attorney, Agent, or Firm* — Pabst Patent Group LLP

(57) ABSTRACT

Antimicrobial compositions including a cell penetrating peptide (CPP) having the amino acid sequence Tyr-Ala-Arg-Val-Arg-Arg-Arg-Gly-Pro-Arg-Gly-Tyr-Ala-Arg-Val-Arg-Arg-Arg-Gly-Pro-Arg-Arg (SEQ ID NO:1) or variant thereof are disclosed. The CPP, which itself has antimicrobial properties, can be advantageously combined with or conjugated to a cargo to increase the delivery, efficacy, or combinations thereof, of the cargo into cells. In preferred embodiments, the CPP is combined with or conjugated to a functional nucleic acid, such as an external guide sequence (EGS) which can target and reduce expression of essential microbial genes or genes than impart resistance to antimicrobial drugs. Methods of using the compositions alone or in combination with traditional antimicrobial drugs to treat infections are also disclosed.

14 Claims, 4 Drawing Sheets

(56) References Cited

OTHER PUBLICATIONS

Dvorin, et al., "A plant-like kinase in Plasmodium falciparum regulates parasite egress from erythrocytes", Science, 328(5980):910-2 (2010).
El Bissati, et al., "The plasma membrane permease PfNT1 is essential for purine salvage in the human malaria parasite Plasmodium falciparum", PNAS, 103(24):9286-91 (2006).
Farrell, et al., "A DOC2 protein identified by mutational profiling is essential for apicomplexan parasite exocytosis", Science, 335(6065):218-21 (2012).
Flatschart and Sogayar, "Functional analysis of newly discovered growth control genes: experimental approaches", Braz. J. Med. Biol. Res., 32(7) 867-75 (1999).
Forster and Altman, "External guide sequences for an RNA enzyme", Science, 249:783-6 (1990).
Gratton, et al.,"Cell-permeable peptides improve cellular uptake and therapeutic gene delivery of replication-deficient viruses in cells and in vivo", Nat. Med., 9:357-62 (2003).
Greenberg et al., "Antisense phosphorodiamidate morpholino oligomers targeted to an essential gene inhibit Burkholderia cepacia complex", J Infect Dis, 201:1822-30 (2010).
Guerrier-Takada, et al., "Phenotypic conversion of drug-resistant bacteria to drug sensitivity", PNAS, 94: 8468-72 (1997).
Guerrier-Takada and Altman, "Inactivation of gene expression using ribonuclease P and external guide sequences", Methods Enzymol, 313:442-56 (2000).
Huang, et al., "Functional silencing of hepatic microsomal glucose-6-phosphatase gene expression in vivo by adenovirus-mediated delivery of short hairpin RNA", FEBS Lett., 558(1-3):69-73 (2004).
Huter, et al., "TGF-beta-induced Foxp3+ regulatory T cells rescue scurfy mice", Eur. J. Immunol. 38:1814-21 (2008).
Jepsen, et al., "Locked nucleic acid: a potent nucleic acid analog in therapeutics and biotechnology" , Oligonucleotides, 14:130-46 (2004).
Jiang, et al., "Effective inhibition of cytomegalovirus infection by external guide sequences in mice" , PNAS, 109(32):13070-5 (2012).
Joet, et al., Acta Trop. Feb. 2004;89(3):371-4, "The hexose transporter of Plasmodium falciparum is a worthy drug target", Acta Trop., 89(3):371-4 (2004).
Joet, et al., "Validation of the hexose transporter of Plasmodium falciparum as a novel drug target.", PNAS, 100(13):7476-9 (2003).
Kim and Liu, "Inhibition of gene expression in human cells using RNase P-derived ribozymes and external guide sequences", Biochim Biophys Acta., 1769(11-12): 603-12 (2007).
Kirk, et al., Curr Drug Targets, "Targeting nutrient uptake mechanisms in Plasmodium", 8(1):75-88 (2007).
Kirk, et al., "Plasmodium permeomics: membrane transport proteins in the malaria parasite", Curr Top Microbiol Immunol., 295:325-56 (2005).
Kirk, "Membrane transport in the malaria-infected erythrocyte", Physiol Rev., 81(2):495-537 (2001).
Lanford , et al., "Therapeutic silencing of microRNA-122 in primates with chronic hepatitis C virus infection", Science, 327:198-201 (2010).
Liu and Altman, "Requirements for cleavage by a modified RNase P of a small model substrate", Nucleic Acids Res., 24(14):2690-6 (1996).
Llopis, et al., "Spatial organization of the flow of genetic information in bacteria", Nature, 466: 77-81 (2010).
Lundblad, et al., "Rapid selection of accessible and cleavable sites in RNA by *Escherichia coli* RNase P and random external guide sequences", PNAS, 105:2354-7 (2008).
Ma, et al., "Intracellular mRNA cleavage induced through activation of RNase P by nuclease-resistant external guide sequences", Nat. Biotechnol. 18(1):58-61 (2000).
Ma, et al., "Nuclease-resistant external guide sequence-induced cleavage of target RNA by human ribonuclease P", Antisense Nucleic Acid Drug Dev., 8:415-26 (1998).

Martin, et al., "Membrane transport proteins of the malaria parasite", Mol Microbiol., 74(3):519-28 (2009).
Martin, et al., "The 'permeome' of the malaria parasite: an overview of the membrane transport proteins of Plasmodium falciparum", Genome Biol., 6(3):R26 (2005).
Mathews, et al., "Incorporating chemical modification constraints into a dynamic programming algorithm for prediction of RNA secondary structure", PNAS, 101 (19):7287-92 (2004).
McClain, et al., "Model substrates for an RNA enzyme", Science, 238:527-30 (1987).
McKinney, et al., "Inhibition of *Escherichia coli* viability by external guide sequences complementary to two essential genes", PNAS, 98:6605-10 (2001).
Meissner, et al., "Tetracycline analogue-regulated transgene expression in Plasmodium falciparum blood stages using Toxoplasma gondii transactivators", PNAS, 102(8)2980-85 (2005).
Mellbye, et al., "Cationic phosphorodiamidate morpholino oligomers efficiently prevent growth of *Escherichia coli* in vitro and in vivo.", J. Antimicrob. Chemoth., 65:98-106 (2010).
Mellbye, et al., "Variations in amino acid composition of antisense peptide-phosphorodiamidate morpholino oligomer affect potency against *Escherichia coli* in vitro and in vivo", Antimicrob Agents Chemother., 53:525-30 (2009).
Morris, et al., "A peptide carrier for the delivery of biologically active proteins into mammalian cells", Nat. Biotechnol., 19:1173-6 (2001).
Muralidharan, et al., "Asparagine repeat function in a Plasmodium falciparum protein assessed via a regulatable fluorescent affinity tag", PNAS, 108 (11):4411-6 (2011).
Nyce and Metzger, "DNA antisense theraphy for asthma in an animal model", Nature, 385:721-5 (1997).
Oh, et al., "A highly effective and long-lasting inhibition of miRNAs with PNA-based antisense oligonucleotides", Mol. Cell, 28:341-5 (2009).
Rothbard, et al., "Conjugation of arginine oligomers to cyclosporin A facilitates topical delivery and inhibition of inflammation", Nat. Med., 6:1253-7 (2000).
Russo, et al., "A calpain unique to alveolates is essential in Plasmodium falciparum and its knockdown reveals an involvement in pre-S-phase development", PNAS,106(5):1554-9 (2009).
Saliba, et al., "Nutrient acquisition by intracellular apicomplexan parasites: staying in for dinner", Int J Parasitol., 31(12):1321-30 (2001).
Schwarze, et al., "In vivo protein transduction: delivery of a biologically active protein into the mouse", Science, 285:1569-72 (1999).
Shen, et al., "Inactivation of expression of several genes in a variety of bacterial species by EGS technology", PNAS, 106:8163-8 (2009).
Slavic, et al., "Life cycle studies of the hexose transporter of Plasmodium species and genetic validation of their essentiality", Mol Microbiol 75(6):1402-13 (2010).
Sliusarenko, et al., "High-throughput, subpixel precision analysis of bacterial morphogenesis and intracellular spatio-temporal dynamics", Molecular Microbiology, 80: 612-27 (2011).
Soler, et al., "Inhibition of aac(6')-lb-mediated amikacin resistance by nuclease-resistant external guide sequences in bacteria", PNAS, 106:13230-5 (2009).
Sterchak, et al., "Uncharged stereoregular nucleic acid analogs. 1. Synthesis of a cytosine-containing oligomer with carbamate internucleoside linkages", Organic Chem., 52:4202-6 (1987).
Talbot, et al., "Gel retardation analysis of the interaction between C5 protein and M1 RNA in the formation of the ribonuclease P holoenzyme from *Escherichia coli*", Biochemistry, 33: 1399-1405 (1994).
Tilley, et al., "Antisense peptide-phosphorodiamidate morpholino oligomer conjugate: dose-response in mice infected with *Escherichia coli*", J Antimicrob Chemother, 59:66-73 (2007).
Trager, et al., "Human malaria parasites in continuous culture", Science, 193 (4254):673-5 (1976).

(56) References Cited

OTHER PUBLICATIONS

Trang, et al., "A ribozyme derived from the catalytic subunit of RNase P from *Escherichia coli* is highly effective in inhibiting replication of herpes simplex virus 1", J. Mol. Biol., 25;301(4):817-26 (2000).

Ullu, et al., "RNA interference in protozoan parasites", Cell Microbiol., 6(6):509-19 (2004).

Wang, "Cellular roles of DNA topoisomerases: a molecular perspective", Nat Rev Mol Cell Biol., 3:430-40 (2002).

Warren, et al., "Advanced antisense therapies for postexposure protection against lethal filovirus infections", Nature Medicine, 16:991-4 (2010).

Wegscheid, et al., "The precursor tRNA 3'-CCA interaction with *Escherichia coli* RNase P RNA is essential for catalysis by RNase P in vivo", RNA, 12:2135-48 (2006).

Wesolowski, et al., "Basic peptide-morpholino oligomer conjugate that is very effective in killing bacteria by gene-specific and nonspecific modes", PNAS, 108(40):16582-7 (2011).

Witola, et al., "Disruption of the Plasmodium falciparum PfPMT gene results in a complete loss of phosphatldylcholine biosynthesis via the serine-decarboxylase-phosphoethanolamine-methyltransferase pathway and severe growth and survival defects", J Biol Chem., 283(41):27636-43 (2008).

Xiao, et al., "Morpholino oligonucleotides do not participate perfectly in standard Watson-Crick complexes with RNA", RNA, 16(11):2218-25 (2010).

Yonekura, et al., "Antisense display—a method for functional gene screening: evaluation in a cell-free system and isolation of angiogenesis-related genes", NAR, 27(13):2591-2600 (1999).

Yuan, et al., "Targeted cleavage of mRNA by human RNase P", PNAS, 89:8006-10 (1992).

Yuan and Altman, "Selection of guide sequences that direct efficient cleavage of mRNA by human ribonuclease P", Science, 263(5151):1269-73 (1994).

Zhu, et al., "Effective inhibition of Rta expression and lytic replication of Kaposi's sarcoma-associated herpesvirus by human RNase P", PNAS, 101(24):9073-8 (2004).

Zuker, "Mfold web server for nucleic acid folding and hybridization prediction", Nucleic Acids Res., 31(13):3406-15 (2003).

\* cited by examiner

Synthesis of CPP conjugated PMO

```
                        SEQUENCE LISTING

<160> NUMBER OF SEQ ID NOS: 54

<210> SEQ ID NO 1
<211> LENGTH: 22
<212> TYPE: PRT
<213> ORGANISM: Artificial Sequence
<220> FEATURE:
<223> OTHER INFORMATION: Synthetic cell penetrating peptide

<400> SEQUENCE: 1

Tyr Ala Arg Val Arg Arg Arg Gly Pro Arg Gly Tyr Ala Arg Val Arg
1               5                   10                  15

Arg Arg Gly Pro Arg Arg
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic cell penetrating peptide

<400> SEQUENCE: 2

Tyr Ala Arg Val Arg Arg Arg Gly Pro Arg Gly Tyr Ala Arg Val Arg
1               5                   10                  15

Arg Arg Gly Pro Arg Arg Cys
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
```

```
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 3

Tyr Ala Xaa Val Xaa Xaa Xaa Gly Pro Xaa Gly Tyr Ala Xaa Val Xaa
1               5                   10                  15

Xaa Xaa Gly Pro Xaa Xaa
            20

<210> SEQ ID NO 4
<211> LENGTH: 13
<212> TYPE: DNA
<213> ORGANISM: Escherichia coli

<400> SEQUENCE: 4
cggtcagggt aac                                                         13

<210> SEQ ID NO 5
<211> LENGTH: 13
<212> TYPE: DNA
<213> ORGANISM: Acinetobacter

<400> SEQUENCE: 5
cggtcagggc aac                                                         13

<210> SEQ ID NO 6
<211> LENGTH: 13
<212> TYPE: DNA
<213> ORGANISM: Bacillus subtilis

<400> SEQUENCE: 6
cggtcacgga aac                                                         13

<210> SEQ ID NO 7
<211> LENGTH: 13
<212> TYPE: DNA
<213> ORGANISM: Enterobacter cloacae

<400> SEQUENCE: 7
tggccagggt aac                                                         13

<210> SEQ ID NO 8
<211> LENGTH: 13
<212> TYPE: DNA
<213> ORGANISM: Enterococcus faecalis

<400> SEQUENCE: 8
cggccacgga aac                                                         13

<210> SEQ ID NO 9
<211> LENGTH: 12
<212> TYPE: DNA
<213> ORGANISM: Klebsiella pneumonia

<400> SEQUENCE: 9
cggcagggta ac                                                          12
```

<210> SEQ ID NO 10

<400> SEQUENCE: 10

000

<210> SEQ ID NO 11

<400> SEQUENCE: 11

000

<210> SEQ ID NO 12
<211> LENGTH: 13
<212> TYPE: DNA
<213> ORGANISM: Salmonella enterica ssp. typhimurium

<400> SEQUENCE: 12
tggtcagggt aac                                                        13

<210> SEQ ID NO 13
<211> LENGTH: 13
<212> TYPE: DNA
<213> ORGANISM: Staphylococcus aureus

<400> SEQUENCE: 13
tggccaaggt aac                                                        13

<210> SEQ ID NO 14
<211> LENGTH: 17
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(17)
<223> OTHER INFORMATION: "T" (thymine) can be substituted for "U" (uracil).
<220> FEATURE:
<221> NAME/KEY: MISC
<222> LOCATION: (1)..(17)
<223> OTHER INFORMATION: "U" (Uracil) can be substituted for "T" (Thymine)

<400> SEQUENCE: 14
gttaccctga ccgacca                                                    17

<210> SEQ ID NO 15
<211> LENGTH: 19
<212> TYPE: DNA
<213> ORGANISM: E. coli

<400> SEQUENCE: 15
cggtcagggt aacttcggt                                                  19

<210> SEQ ID NO 16
<211> LENGTH: 19
<212> TYPE: DNA
<213> ORGANISM: P. falciparum

<400> SEQUENCE: 16
aggttatggt aatttggt                                                   19

<210> SEQ ID NO 17
<211> LENGTH: 19

```
<212> TYPE: DNA
<213> ORGANISM: P. yoelli

<400> SEQUENCE: 17
tggatatggt aattttggg                                                  19

<210> SEQ ID NO 18
<211> LENGTH: 19
<212> TYPE: DNA
<213> ORGANISM: P. berghei

<400> SEQUENCE: 18
cggatatggt aattttgga                                                  19

<210> SEQ ID NO 19
<211> LENGTH: 19
<212> TYPE: DNA
<213> ORGANISM: Homo sapiens

<400> SEQUENCE: 19
tgattattat aattttgag                                                  19

<210> SEQ ID NO 20
<211> LENGTH: 36
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(36)
<223> OTHER INFORMATION: "T" (thymine) can be substituted for "U"
      (Uracil)

<400> SEQUENCE: 20
gaaguacgaa gguucgaauc cuuccccug acuggu                                36

<210> SEQ ID NO 21
<211> LENGTH: 33
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(33)
<223> OTHER INFORMATION: "T" (thymine) can be substituted for "U"
      (Uracil)

<400> SEQUENCE: 21
gaaguacgag guucgaaucc uccccugacu ggu                                  33

<210> SEQ ID NO 22
<211> LENGTH: 36
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(36)
<223> OTHER INFORMATION: "T" (thymine) can be substituted for "U"
      (uracil)

<400> SEQUENCE: 22
gaaauacgaa gguucgaauc cuuccccaua acuggu                               36
```

```
<210> SEQ ID NO 23
<211> LENGTH: 33
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(33)
<223> OTHER INFORMATION: "U" (uracil) can be substituted for "T"
      (thymine)

<400> SEQUENCE: 23
gaaauacgag guucgaaucc ucccauaacu ggu                              33

<210> SEQ ID NO 24
<211> LENGTH: 33
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(33)
<223> OTHER INFORMATION: "T" (thymine) can be substituted for "U"
      (uracil)

<400> SEQUENCE: 24
gaaauacgag guucgugccc ucccauaacu ggu                              33

<210> SEQ ID NO 25
<211> LENGTH: 31
<212> TYPE: RNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(31)
<223> OTHER INFORMATION: "T" (thymine) can be substituted for "U"
      (uracil)

<400> SEQUENCE: 25
gaaauacgag guucgaccuc ccauaacugg u                                31

<210> SEQ ID NO 26
<211> LENGTH: 20
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(20)
<223> OTHER INFORMATION: "U" (uracil) can be substituted for "T"
      (thymine)

<400> SEQUENCE: 26
ctgactgaaa tgcctcacca                                             20

<210> SEQ ID NO 27
<211> LENGTH: 19
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (11)..(11)
<223> OTHER INFORMATION: "U" (uracil) can be substituted for "T"
      (thymine)
```

```
<400> SEQUENCE: 27
gaccgccgag tcaccacca                                                19

<210> SEQ ID NO 28
<211> LENGTH: 14
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (5)..(5)
<223> OTHER INFORMATION: "U" (uracil) can be substituted for "T"
      (thymine)

<400> SEQUENCE: 28
accctgaccg acca                                                     14

<210> SEQ ID NO 29
<211> LENGTH: 11
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (2)..(2)
<223> OTHER INFORMATION: "U" (uracil) can be substituted for "T"
      (thymine)

<400> SEQUENCE: 29
ctgaccgacc a                                                        11

<210> SEQ ID NO 30
<211> LENGTH: 16
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (3)..(5)
<223> OTHER INFORMATION: "U" (uracil) can be substituted for "T"
      (thymine)

<400> SEQUENCE: 30
ggtttgaggg acacca                                                   16

<210> SEQ ID NO 31
<211> LENGTH: 16
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(1)
<223> OTHER INFORMATION: "U" (uracil) can be substituted for "T"
      (thymine)

<400> SEQUENCE: 31
taagggcgac acacca                                                   16

<210> SEQ ID NO 32
<211> LENGTH: 18
<212> TYPE: DNA
<213> ORGANISM: Artificial Sequence
<220> FEATURE:
```

```
<223> OTHER INFORMATION: Synthetic morpholino oligonucleotide
<220> FEATURE:
<221> NAME/KEY: MISC
<222> LOCATION: (1)..(18)
<223> OTHER INFORMATION: "U" (uracil) can be substituted for "T"
      (thymine)

<400> SEQUENCE: 32
ctgttcacta gcttgcaa                                                        18

<210> SEQ ID NO 33
<211> LENGTH: 5
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(5)
<223> OTHER INFORMATION: "U" (uracil) can be substituted for "T"
      (thymine)

<400> SEQUENCE: 33 ctagc                                                                       5

<210> SEQ ID NO 34
<211> LENGTH: 9
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(9)
<223> OTHER INFORMATION: "U" (uracil) can be substituted for "T"
      (thymine)

<400> SEQUENCE: 34 cactagctt                                                                   9

<210> SEQ ID NO 35
<211> LENGTH: 13
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(13)
<223> OTHER INFORMATION: "U" (uracil) can be substituted for "T"
      (thymine)

<400> SEQUENCE: 35
ttcactagct tgc                                                             13

<210> SEQ ID NO 36
<211> LENGTH: 11
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (1)..(11)
<223> OTHER INFORMATION: "U" (uracil) can be substituted for "T"
      (thymine)

<400> SEQUENCE: 36
tttttttttt t                                                               11
```

```
<210> SEQ ID NO 37
<211> LENGTH: 17
<212> TYPE: DNA
<213> ORGANISM: Artificial Sequence
<220> FEATURE:
<223> OTHER INFORMATION: Synthetic morpholino oligonucleotide
<220> FEATURE:
<221> NAME/KEY: MISC
<222> LOCATION: (4)..(4)
<223> OTHER INFORMATION: "U" (uracil) can be substituted for "T"
      (thymine)
<220> FEATURE:
<221> NAME/KEY: MISC
<222> LOCATION: (12)..(12)
<223> OTHER INFORMATION: "U" (uracil) can be substituted for "T"
      (thymine)

<400> SEQUENCE: 37
cggtgcgggc ctcacca                                                   17

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide

<400> SEQUENCE: 38

Tyr Ala Arg Val Arg Arg Arg Gly Pro Arg Arg
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

Gly Pro Arg Gly Tyr Ala Arg Val Arg Arg Arg Gly Pro Arg Arg
1               5                   10                  15

<210> SEQ ID NO 40
<211> LENGTH: 19
<212> TYPE: PRT
<213> ORGANISM: Artificial Sequence
<220> FEATURE:
<223> OTHER INFORMATION: Synthetic peptide

<400> SEQUENCE: 40

Val Arg Arg Arg Gly Pro Arg Gly Tyr Ala Arg Val Arg Arg Arg Gly
1               5                   10                  15

Pro Arg Arg

<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Tyr Ala Arg Val Arg Arg Arg Gly Pro Arg Gly Tyr Ala Arg
1               5                   10

<210> SEQ ID NO 42
```

```
<400> SEQUENCE: 42

000

<210> SEQ ID NO 43
<211> LENGTH: 21
<212> TYPE: DNA
<213> ORGANISM: Artificial Sequence
<220> FEATURE:
<223> OTHER INFORMATION: Synthetic primer

<400> SEQUENCE: 43
aaagaagcaa gcaggaatcc a                                              21

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
tgatggtgca agggttgtaa                                                20

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
tcatccacac ggtgataaga g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
gctgcagcgt tatattcaac a                                              21

<210> SEQ ID NO 47
<211> LENGTH: 28
<212> TYPE: DNA
<213> ORGANISM: Artificial Sequence
<220> FEATURE:
<223> OTHER INFORMATION: Synthetic EGS sequence
<220> FEATURE:
<221> NAME/KEY: MISC
<222> LOCATION: (1)..(27)
<223> OTHER INFORMATION: "U" (uracil) can be substituted for "T"
      (thymine), and "T" (thymine) can be substituted for "U" (Uracil)

<400> SEQUENCE: 47
aaatacgagg uucgaauccu cccauaac                                       28

<210> SEQ ID NO 48
<211> LENGTH: 13
<212> TYPE: RNA
<213> ORGANISM: Artificial Sequence
<220> FEATURE:
<223> OTHER INFORMATION: Synthetic plfgyr mRNA fragment

<400> SEQUENCE: 48
```
guuaugguaa uuu                                                                 13

<210> SEQ ID NO 49
<211> LENGTH: 23
<212> TYPE: PRT
<213> ORGANISM: Artificial Sequence
<220> FEATURE:
<223> OTHER INFORMATION: Synthetic cell penetrating peptide

<400> SEQUENCE: 49

Tyr Ala Arg Val Arg Arg Arg Gly Pro Arg Arg Gly Tyr Ala Arg Val
1               5                   10                  15

Arg Arg Arg Gly Pro Arg Arg
            20

<210> SEQ ID NO 50
<211> LENGTH: 24
<212> TYPE: PRT
<213> ORGANISM: Artificial Sequence
<220> FEATURE:
<223> OTHER INFORMATION: Synthetic cell penetrating peptide

<400> SEQUENCE: 50

Tyr Ala Arg Val Arg Arg Arg Gly Pro Arg Gly Tyr Ala Arg Val
1               5                   10                  15

Arg Arg Arg Gly Pro Arg Arg Cys
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid

<400> SEQUENCE: 51

Tyr Ala Xaa Val Xaa Xaa Xaa Gly Pro Xaa Gly Tyr Ala Xaa Val Xaa
1               5                   10                  15

Xaa Xaa Gly Pro Xaa Xaa Cys
            20

<210> SEQ ID NO 52
<211> LENGTH: 23
<212> TYPE: PRT
<213> ORGANISM: Artificial Sequence

```
<220> FEATURE:
<223> OTHER INFORMATION: Synthetic cell penetrating peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid

<400> SEQUENCE: 52

Tyr Ala Xaa Val Xaa Xaa Xaa Gly Pro Xaa Xaa Gly Tyr Ala Xaa Val
1               5                   10                  15

Xaa Xaa Xaa Gly Pro Xaa Xaa
            20

<210> SEQ ID NO 53
<211> LENGTH: 24
<212> TYPE: PRT
<213> ORGANISM: Artificial Sequence
<220> FEATURE:
<223> OTHER INFORMATION: Synthetic cell penetrating peptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid

<400> SEQUENCE: 53

Tyr Ala Xaa Val Xaa Xaa Xaa Gly Pro Xaa Xaa Gly Tyr Ala Xaa Val
1               5                   10                  15

Xaa Xaa Xaa Gly Pro Xaa Xaa Cys
            20

<210> SEQ ID NO 54
<211> LENGTH: 28
<212> TYPE: DNA
```

```
<213> ORGANISM: Artificial Sequence
<220> FEATURE:
<223> OTHER INFORMATION: Synthetic Plfgyr2 EGS
<220> FEATURE:
<221> NAME/KEY: MISC
<222> LOCATION: (1)..(28)
<223> OTHER INFORMATION: "U" (uracil) can be substituted for "T"
      (thymine), and "T" (thymine) can be substituted for "U" (Uracil)

<400> SEQUENCE: 54
aaatacgagg uucgtgcccu cccauaac                                      28
```

ANTIMICROBIAL COMPOSITIONS AND METHODS OF USE THEREOF

CROSS REFERENCE TO RELATED APPLICATIONS

This application is a 371 application of International Application No. PCT/US2012/056687, filed Sep. 21, 2012, which claims the benefit of and priority to U.S. Provisional Application No. 61/537,326, entitled "Novel Compounds for Treatment of Bacterial Infections" filed Sep. 21, 2011, and U.S. Provisional Application No. 61/590,062 entitled "A New Drug for Malaria".

STATEMENT REGARDING FEDERALLY SPONSORED RESEARCH OR DEVELOPMENT

This invention was made with government support under Agreement Nos, AI51507 awarded by the National Institute of Allergy and Infectious Diseases, R33 CA118631, R01 GM065835, and AI041927 awarded by the National Institutes of Health. The government has certain rights in the invention.

REFERENCE TO SEQUENCE LISTING

The Sequence Listing submitted as a text file named "YU_5549_5740_PCT_2_ST25.txt," created on Jun. 22, 2017, and having a size of 19,742 bytes is hereby incorporated by reference.

FIELD OF THE INVENTION

The invention is general drawn to the field of antimicrobial compositions and methods of use thereof.

BACKGROUND OF THE INVENTION

Antimicrobial resistance is the response of microbes to the selective pressure of an antimicrobial drug therapy. Concerns over increased resistance and the emergence of multidrug resistant strains of gram-negative bacteria (Pseudomonas, *Klebsiella, Enterobacter, Acinetobacter, Salmonella* species) and gram-positive organisms (*Staphylococcus, Enterococcus, Streptococcus* species) have resulted in an increased number of reports encouraging a reduction in the use of antibacterials, appropriate choice of antibacterials and regimens, prevention of cross-infection and development of new antibacterials (Sharma, et al., *Indian J Med. Sci.* 9(3):120-9 (2005)). Resistance to some antimicrobial drugs can be overcome by modifying the dosage regimens (e.g., using high-dose therapy) or inhibiting the resistance mechanism (e.g., beta-lactamase inhibitors), whereas other mechanisms of resistance can only be overcome by using an agent from a different class.

Malaria, for example, is the most prevalent and deadliest parasitic disease worldwide (Anonymous, World Malaria Report. (World Health Organization) (2010) (Murray, et al., *Lancet,* 379(9814):413-431 (2012)). Although once eradicated in many developed countries, malaria is reemerging and spreading in to new areas, such as Central Asia, and Eastern Europe. More people are now dying of malaria than thirty years ago (Malaria Foundation International, malaria.org). Although the traditional drug regime of chloroquine is safe and inexpensive, resistance to the drug is high or on the rise in Asia, and parts of Africa and South America. In some areas of Asia there is resistance to all the major drugs.

Malaria is caused by intraerythrocytic protozoan parasites of the genus *Plasmodium*. Four species, *P. falciparum, P. vivax, P. malariae* and *P. ovale* are known to be infectious to humans, and more recent cases of infection due to *P. knowlesi* have also been reported (Singh, et al., *Lancet* 363(9414):1017-1024 (2004)). The lack of a universally effective vaccine to combat this disease and the growing spread of resistance to all currently known antimalarials, including those used in combination therapy, emphasize the need for new approaches to develop new therapies that specifically target essential functions of the parasite to block both infection and transmission.

The genome of *P. falciparum* has 23 Mb and encodes approximately 5300 proteins, the majority of which are of unknown function and their importance in parasite development remains to be determined. This is due mostly to the difficulty of genetically manipulating this organism using forward genetic approaches, lack of a RNAi machinery and absence of regulatable promoters. Current techniques for genetic disruption are mostly useful for those genes that are not essential for blood stage development (Ullu, et al., *Cell Microbiol* 6(6):509-519 (2004) El Bissati, et al., *Proc Natl Acad Sci USA* 103(24):9286-9291 (2006)). Consequently, only a limited number of genes have been shown through genetic means to play an essential role in parasite development and thus are valid targets for development of new antimalarial drugs. Nutritional complementation has recently been used to generate a conditionally lethal *P. falciparum* mutant lacking the primary purine transporter PfNT1 (El Bissati, et al., *Proc Natl Acad Sci USA* 103(24):9286-9291 (2006)). However, this approach cannot be used widely to create conditionally lethal mutants. Although new methods for inducible expression have been reported, they have had limited success in creating stably inducible knockouts (Armstrong, et al., *Nat Methods* 4(12):1007-1009 (2007), Meissner, et al., *Proc Natl Acad Sci USA* 102(8):2980-2985 (2005), Muralidharan, et al., *Proc Natl Acad Sci USA* 108(11):4411-4416 (2011), Russo, et al., *Proc Natl Acad Sci USA* 106(5):1554-1559 (2009), Dvorin, et al., *Science* 328(5980):910-912 (2010), Farrell, et al., *Science* 335(6065):218-221 (2012)).

One class of compounds under investigation as a complement or alternative to small molecule antimicrobial drugs is inhibitory nucleic acids. Several inhibitory nucleic acid methods involving RNA, or some chemically modified form of RNA or DNA (siRNA, hammerhead RNA, antisense RNA, LNA or PNA) are being employed in attempts to inhibit the expression of genes, including essential microbial genes, or drug resistance genes in vivo. Among these are basic peptide-morpholino oligonucleotide conjugates. Some practical success has been observed, in particular, in terms of treating mice infected with bacteria and prevention of infection of mammalian tissue by dangerous viruses (Jepsen et al., 14:130-46 (2004), Oh et al., *Mol. Cell.* 28:341-345 (2009), Lanford et al., *Science* 327:198-201 (2010), Mellbye et al., *Antimicrob Agents Chemother* 53:525-530 (2009), Tilley et al., *Escherichia coli. J Antimicrob Chemother* 59:66-73 (2007), Warren et al., *Nature Medicine* 16:991-994 (2010), Soler et al., *Proc Natl Acad Sci USA* 106:13230-13235 (2009), Mellbye et al., *J. Antimicrob. Chemoth.* 65:98-106 (2010), Greenberg et al., *J Infect Dis* 201:1822-1830 (2010)). Despite these limited successes, there is a need to improve the safety and efficacy of inhibitory nucleic acid strategies before they can be successfully translated to the clinic.

Accordingly, it is an object of the invention to provide improved inhibitory nucleic acids with greater efficacy that can be used at a lower dosage.

It is also an object of the invention to provide alternative compositions and methods for treating microbial infections, particularly drug resistant infections such as malaria.

It is another object of the present invention to provide compositions for preventing development of drug resistance in bacteria and parasites such as malaria.

It is also an object of the invention to provide compositions and methods for functional analysis of microbial genomes, such as those of *Plasmodium*.

SUMMARY OF THE INVENTION

Antimicrobial compositions that typically include a cell penetrating peptide (CPP) having the amino acid sequence Tyr-Ala-Arg-Val-Arg-Arg-Arg-Gly-Pro-Arg-Gly-Tyr-Ala-Arg-Val-Arg-Arg-Arg-Gly-Pro-Arg-Arg (SEQ ID NO:1), or variant thereof, which may have antimicrobial properties, have been designed to enhance delivery of external guide sequences ("EGS"). The CPP can be advantageously combined with or conjugated to a cargo to increase the delivery, efficacy, or combinations thereof, of the cargo into cells. In preferred embodiments, the CPP is combined with or conjugated to an EGS oligonucleotide which targets and reduces expression of an essential microbial gene(s) or gene(s) than impart resistance to an antimicrobial drug. EGS take advantage of endogenous RNAse P in bacterial cells, or the eukaryotic equivalent in parasitic cells, to cleave essential RNA in the organisms, thereby killing, preventing proliferation, or development of drug resistance.

The external guide sequence (EGS) can be specific for a target gene, or can be non-specific, for example, a randomly generated or scrambled sequence. In preferred embodiments, the EGS oligonucleotide is chemically modified to improve its stability within a cell. The oligonucleotide can be a morpholino oligonucleotide, for example, a phosphorodiamidate morpholino oligonucleotide (PMO).

Methods of using the compositions to regulate gene expression are disclosed. For example, when contacted with a cell, the CPP used in combination with, or conjugated to, an oligonucleotide that silences gene expression can be used to reduce, decrease, inhibit, or silence expression of the target gene.

Methods of reducing the viability or proliferation of microorganisms are also disclosed. In some embodiments, microorganisms are contacted with the CPP alone, in combination with, or conjugated to, an oligonucleotide. In some embodiments, the oligonucleotide includes an EGS that prevents expression of a gene of the microorganism, such as an essential gene of the microorganism for viability, proliferation, or infection, an antimicrobial resistant gene. The compositions can include two or more EGS that bind two different target sequences. The target sequences can be part of the same gene sequence, or can be from two different genes.

Accordingly, in some embodiments, a composition that includes a CPP conjugated to a PMO that targets a specific essential gene in a microorganism, an antimicrobial resistance gene harbored by the microorganism, or a combination thereof, are contacted with the microorganism in an effective amount to reduce the viability of the microorganism relative to a control. EGS target sequences and PMO external guide sequences designed to target essential genes or antimicrobial resistance genes in various microorganisms are also disclosed. As discussed in more detail below, in some embodiments, the CPP provides a mechanism of transporting the sequence of bases in the PMO into bacteria where the external guide sequence (EGS) methodology allows the breakage of the target RNA by the resident RNase P.

Methods of treating microbial infections are disclosed. The methods can include administrating a composition including a CPP alone, in combination with, or conjugated to an oligonucleotide to a subject in need thereof in an effective amount to reduce one or more symptoms of a disease caused by a microorganism in the subject. For example, the methods can be used to treat a bacterial or parasitic infection, such as malaria. In some embodiments, the oligonucleotide is one or more EGSs that specifically target one or more genes of the microorganism. The gene can be an essential gene or an antimicrobial resistance gene, or a combination thereof. This combination of CPP and EGS induces killing targeted bacteria or parasites at concentrations of conjugate at least ten-fold lower than compositions previously used.

In some embodiments, the compositions reduce expression of a gene or genes in the microorganism, and do not reduce gene expression of a host gene or genes. The composition including a CPP alone, in combination with, or conjugated to an oligonucleotide, can be administered with a traditional antimicrobial, such as antibiotic or antiparasitic compound. In some embodiments, a CPP in combination with or conjugated to an oligonucleotide that reduces expression of an antimicrobial resistance gene, is co-administered in combination with the antimicrobial agent to which the gene imparts resistance.

The compositions can also be used prevent or reduce institutional or iatrogenic infections. For example, the compositions can be coated onto a surgical device or medical device to prevent, reduce, decrease, or inhibit the occurrence of institutional or opportunistic infections that are acquired during or as a result of a surgical procedure. For examples, the compositions can be implanted in or coated on surgical or medical devices before or during introduction of the device into the patient. The composition can be designed for sustained or controlled release following implantation. Preferred examples include catheters, and vascular valves, stents or grafts, or other devices that are permanently, semi-permanently or temporarily introduced into the patient. The compositions can also be used in a wound dressing. For example, the compositions can be applied to damaged, diseased, or burned tissue, to enhance healing or reduce or prevent infection or a symptom of an infection. The EGS (or PMO) may be provided alone, as a component in a kit with the device for administration at the time of implantation or injection, or in a kit for administration with the antimicrobial.

The compositions including a CPP and an inhibitory nucleic acid can be used for functional gene screening. Methods of functional gene screening using antisense technology have been used to characterize the function of the genes and are known in the art. However, in some organisms such as *P. falciparum*, RNA based antisense methods are ineffective. Therefore the use of compositions including CPP in combination with EGS can be used for functional genomic screening in organisms where screening is not possible using traditional RNA-based antisense reagents. Generally, cells are contacted with the disclosed compositions including a CPP and an inhibitory nucleic acid, such as an EGS, and monitored for a phenotype. The methods can be used to identify essential genes. For example, reduced viability, proliferation, or activity of a cell when contacted with the CPP and an inhibitory nucleic acid, such as an EGS, is indicative that the gene targeted by the inhibitory nucleic acid is an essential gene. The methods can also be used to identify drug resistance genes.

DETAILED DESCRIPTION OF THE INVENTION

I. Definitions

Figure 1:
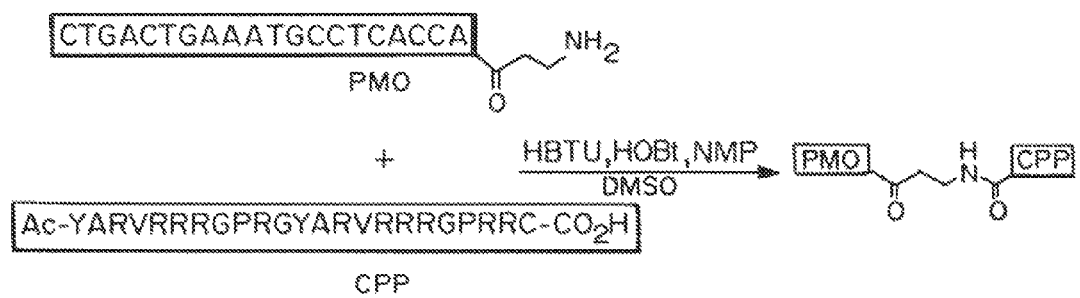
FIG. 1 is a scheme for synthesis of a CPP-PMO conjugate (see Example 1, Materials and Methods) from the PMO SEQ ID NO:2 and the CPP SEQ ID NO:26.

As used herein, the term "antimicrobial" is a substance that kills or inhibits the growth of a microorganism such as bacteria, fungi, protozoans, or parasites.

As used herein, the term "Cell Penetrating Peptide" or "CPP" or "Protein Transduction Domain" or "PTD" refers to a polypeptide, polynucleotide, carbohydrate, or organic or inorganic compounds that facilitates traversing a lipid bilayer, micelle, cell membrane, organelle membrane, or vesicle membrane. A CPP or PTD attached to another molecule facilitates the molecule traversing membranes, for example, going from extracellular space to intracellular space, or cytosol to within an organelle. CPP are often basic peptides characterized by a number of basic amino acid residues, for example arginines.

As used herein, the term "polynucleotide" generally refers to any polyribonucleotide or polydeoxyribonucleotide, or nucleotide analog which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides can be composed of or include locked nucleic acids, peptide nucleic acids, morpholinos, or other nucleotide or nucleoside analogs.

As used herein, the term "oligonucleotide(s)" refers to relatively short polynucleotides. The term can refer to single-stranded deoxyribonucleotides, ribonucleotides, or nucleotide analogs, but it can refer as well to double-stranded ribonucleotides, RNA:DNA hybrids, double-stranded DNAs, double stranded nucleotide analogs and hybrids among others.

As used herein, "inhibitory nucleic acid" or "inhibitory oligonucleotide" refers to an oligonucleotide that can reduce, inhibit, or silence expression of a gene, typically by reducing expression of an mRNA encoded by the gene. Examples of inhibitory nucleic acids include antisense technology including, but not limited to, small interfering RNA (siRNA), RNA interference (RNAi), external guide sequences (EGS). The inhibitory nucleic acids can be RNA, DNA, locked nucleic acids, peptide nucleic acids, morpholinos, or other nucleotide analogs or chemically modified nucleotides or nucleosides.

As used herein, "antisense" or "antisense technology" references an oligonucleotide with a base sequence that is complementary to a target messenger RNA (mRNA), which is called the "sense" sequence. For example, a sense segment of mRNA "5'-AGGUC-3'" would be blocked by the anti-sense mRNA segment "3'-UCCAG-5'").

As used herein, "external guide sequence" or "EGS" refer to any oligonucleotide or oligonucleotide analog that forms, in combination with a target RNA, a substrate for RNAase P, or the RNA subunit thereof.

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

As used herein, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

An "isolated" nucleic acid molecule or polynucleotide is a nucleic acid molecule that is identified and separated from at least one contaminant nucleic acid molecule with which it is ordinarily associated in the natural source. The isolated nucleic can be, for example, free of association with all components with which it is naturally associated. An isolated nucleic acid molecule is other than in the form or setting in which it is found in nature.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "promoter" refers to a regulatory nucleic acid sequence, typically located upstream (5') of a gene or protein coding sequence that, in conjunction with various elements, is responsible for regulating the expression of the gene or protein coding sequence. These include constitutive promoters, inducible promoters, tissue- and cell-specific promoters and developmentally-regulated promoters.

A nucleic acid sequence or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking can be accomplished by ligation at convenient restriction sites. If such sites do not exist, synthetic oligonucleotide adaptors or linkers are used in accordance with conventional practice.

"Transformed," "transgenic," "transfected" and "recombinant" refer to a host organism such as a bacterium, parasite, or eukaryotic cell into which a heterologous nucleic acid molecule has been introduced. The nucleic acid molecule can be stably integrated into the genome of the host or the nucleic acid molecule can also be present as an extra-chromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium, parasite, or eukaryotic cell, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties. In making such changes, the hydropathic index of amino acids can be considered.

Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotide or amino acid sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

The term "suppressed," "silenced," or "decreased" gene expression encompasses the absence of gene expression or encoded protein levels in a cell, as well as gene expression that is present but reduced as compared to the level of gene expression in a wild type or untreated cell. The term "suppressed" also encompasses an amount of a protein that is equivalent to wild type expression of the protein, but where the protein has a reduced level of activity.

Small RNA molecules are single stranded or double stranded RNA molecules generally less than 200 nucleotides in length. Such molecules are generally less than 100 nucleotides and usually vary from 10 to 100 nucleotides in length. In a preferred format, small RNA molecules have 11, 12, 13, 14, 15, 16, 17, 18, 19, 20, 21, 22, 23, 24, 25, 26, 27, 28, 29 or 30 nucleotides. Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Third Edition, Cold Spring Harbor, N.Y. (2000).

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" is used in reference to a vehicle used to introduce a nucleic acid sequence into a cell. A viral vector is virus that has been modified to allow recombinant DNA sequences to be introduced into host cells or cell organelles.

II. Compositions

A. Cell Penetrating Peptides

The terms protein transduction domain (PTD) and cell penetrating peptide (CPP) typically refer to a class of peptides that can cross biological membranes and deliver various cargo molecules, including protein, RNA, and DNA, into all cells. Several PTDs, such as TAT, VP22, Antp, R7, or R9, have been developed as potential drug delivery systems to be used for clinical applications (Schwarze, et al., *Science*, 285:1569-1572 (1999), Gratton, et al., *Nat. Med.*, 9:357-362 (2003), Morris, et al., *Nat. Biotechnol.*, 19:1173-1176 (2001), Bennett, et al., *Nat. Biotechnol.* 20:20 (2002), Rothbard, et al., *Nat. Med.*, 6:1253-1257 (2000), and Huter, et al., *Eur. J. Immunol.* 38:1814-1821 (2008)).

A CPP derived from a protein found in human T cells, with improved properties, has been developed. In some embodiments, the CPP includes the amino acid sequence YARVRRRGPRGYARVRRRGPRR (SEQ ID NO:1) or a variant thereof having one or more amino acid substitutions, insertions, or deletions and at least 90%, 95%, or more sequence identity compared to SEQ ID NO:1. For example, in embodiments the CPP includes the amino acid sequence YARVRRRGPRRGYARVRRRGPRR (SEQ ID NO:49).

In some embodiments, the N-terminal amino acid, the C-terminal amino acids, or combinations thereof are deleted. For example, in some embodiments, the CPP includes the amino sequence YARVRRRGPRGYARVRRRGPRRC (SEQ ID NO:2) or a variant thereof having one or more amino acid substitutions, insertions, or deletions and at least 90%, 95%, or more sequence identity compared to SEQ ID NO:1. For example, in some embodiments, the CPP includes the amino acid sequence YARVRRRGPRRGYARVRRRG-PRRC (SEQ ID NO:50).

In some embodiments, all of the amino acid residues are L-form amino acid residues. In some embodiments, one or more of the amino acids are D-form amino acid residues. For example, 1, 2, 3, 4, 5 or more of the arginine residues can be substituted with the D-form of arginine. Accordingly, in some embodiments, the CPP includes in the sequence YAXVXXXGPXGYAXVXXXGPXX (SEQ ID NO:3), YAXVXXXGPXGYAXVXXXGPXXC (SEQ ID NO:51), YAXVXXXGPXXGYAXVXXXGPXX (SEQ ID NO:52), or YAXVXXXGPXXGYAXVXXXGPXXC (SEQ ID NO:53), wherein X is an L-form arginine residue or a D-form arginine residue.

In some embodiments, a CPP including one or more D-form amino acids exhibits an increase in cell penetrating ability, stability, or retention within the cell compared to the same CPP amino acid sequencing containing fewer or no D-form amino acids.

In some embodiments, three N-terminal amino acids are deleted from SEQ ID NO:1, SEQ ID NO:2, SEQ ID NO:3, SEQ ID NO:49, SEQ ID NO:50, SEQ ID NO:51, SEQ ID NO:52, or SEQ ID NO:53.

In some embodiments, one or more D-form amino acids can be substituted or added at the junction with the inhibitory oligonucleotide. In some embodiments, one or more non-natural amino acid analogs can also be used at the interface. The interface can be at the C-terminal or N-terminal end of the CPP. The interface can be at the 5' or 3' end of the inhibitory nucleic acid.

Methods of conjugating functional nucleic acids, such as morpholino oligonucleotides, are known in the art. See for example, Abes, et al., *J. Control Release*, 116:304-313 (2006), or can be prepared commercially.

In some embodiments, the CPP or CPP-oligonucleotide conjugate is modified to include a label capable of providing a detectable signal, either directly or indirectly, including, but not limited to, radioisotopes, fluorescent, biological and enzymatic compounds. In one embodiment, the CPP is labeled with a fluorescent tag such as a fluorescein.

These CPP exhibits improved properties compared to other art-recognized CPP. For example, when contacted with a microbial cell, for example, a bacterial cell, the CPP can reduce viability of the cell. When used in combination with an inhibitory nucleic acid, such as an external guide sequence, designed to reduce or inhibit expression of a microbial gene, the CPP-oligonucleotide conjugates can be 10, 20, 30, 40, 50, 60, 70, 80, 100, 250, 500, 1000-fold or more than 1000-fold more effective than reported CPP-conjugates at altering a phenotype of the host cell (Shen, et al., *Proc. Natl. Acad. Sci. USA.*, 106:8163-8168 (2009)). For example, in some embodiments, the CPP-oligonucleotide conjugates can be 10, 20, 30, 40, 50, 60, 70, 80, 100, 250, 500, 1000-fold or more than 1000-fold more effective than previously reported CPP-conjugates at reducing or inhibiting expression of a host gene. In some embodiments, the host gene is an essential host gene or antimicrobial resistant gene. In some embodiments, the CPP-oligonucleotide conjugates can be 10, 20, 30, 40, 50, 60, 70, 80, 100, 250, 500, 1000-fold or more than 1000-fold more effective than previously reported CPP-conjugates at reducing viability of or killing the host cell.

In some embodiments, the CPP is a domain or fusion partner of a fusion protein. As used herein, "fusion proteins" and "chimeric proteins" means proteins created through the joining of two or more domains or segments which were originally domains or segments of separate proteins. For example, the CPP can be a first fusion partner fused to a second fusion partner such as a heterologous polypeptide. In some embodiments, the CPP is not a domain or fusion partner of a fusion protein.

B. Oligonucleotides

In some embodiments, the CPP can be used to increase the delivery, efficacy, or combinations thereof, of an oligonucleotide. The oligonucleotide can be covalently or non-covalently linked to the CPP, or the CPP and oligonucleotide can be unlinked.

The oligonucleotide includes an external guide sequence. External guide sequences (EGSs) are molecules that bind a target RNA nucleic acid molecule to form a complex, and this complex targets the RNA for degradation by endogenous RNases such as RNase P. EGS have several unique features over other gene-targeting agents. Targeting with EGS results in irreversible cleavage of the RNA by cellular endogenous RNase P (or its equivalent).

Ribonuclease P (RNase P) is a ribonucleoprotein complex found in all organisms. It is highly active in cells and is responsible for the maturation of 5' termini of all tRNAs, which account for approximately 2% of total cellular RNA. Human RNase P has at least nine polypeptides and a RNA subunit (H1 RNA). One of the unique features of RNase P is its ability to recognize structures, rather than the sequences, of substrates. This allows RNase P to hydrolyze different natural substrates in vivo or in vitro. Accordingly, any complex of two RNA molecules that resembles a fragment of a tRNA molecule can be recognized and cleaved by RNase P. One of the RNA molecules is called the external guide sequence. An mRNA sequence can be targeted for RNase P cleavage by using EGSs to hybridize with the target RNA and direct RNase P to the site of cleavage. The EGS include two sequence elements: a guide sequence complementary to the mRNA sequence and a recognition sequence, which is a portion of the natural tRNA sequence and is required for RNase P recognition.

EGS can be designed that mimics certain structural features of a tRNA molecule when it forms a bimolecular complex with another RNA sequence contained within a cellular messenger RNA (mRNA). Thus, any mRNA can in principle be recognized as a substrate for RNAse P with both the EGS and RNAse P participating as cocatalysts. The EGS guiding bacterial RNAase P is different from the EGS guiding the eukaryotic RNAase P. The latter is longer and requires a T stem and loop structure to promote eucaryotic RNase P recognition. Great specificity in targeting can be achieved by selection of the EGS. For example, a bacterial EGS will only promote cleavage by the bacterial RNAase P in a bacterial cell, not in an eukaryotic cells.

RNAase P is a ribonucleoprotein having two components, an RNA component and a protein component. The RNA component of RNAase P is responsible for the catalytic cleavage which forms the mature 5' ends of all transfer RNAs. RNAase P is endogenous to all living cells that have been examined During the studies on recognition of substrate by RNAase P, it was found that $E.$ $coli$ RNAase P can cleave synthetic tRNA-related substrates that lack certain domains, specifically, the D, T, and anticodon stems and loops, of the normal tRNA structure. The 5' proximal sequence of the RNA helix does not have to be covalently linked to 3' proximal sequence of the helix. The 3' proximal sequence of the stem can be regarded as a guide sequence because it identifies the site of cleavage in the 5' proximal region through a base-paired region.

RNAase P from $E.$ $coli$ and eukaryotic cells have similar but not identical biochemical properties. Their RNA components have similar secondary structures. However, the substrate range of eukaryotic RNAase P is much narrower than that of the $E.$ $coli$ enzyme. Accordingly, EGS designed to target bacterial genes can include feature that allow recognition of the EGS by bacterial RNAase P, while EGS designed to target eukaryotic mRNA, or mRNA from viruses or parasites within a eukaryotic cell or in the presence of a eukaryotic RNAase P, can include features that allow recognition of the EGS by eukaryotic RNAase P.

For example, although $E.$ $coli$ RNAase P can cleave a synthetic tRNA-related substrate that lacks three specific domains (the D, variable, and anticodon stem and loop) of the normal tRNA structure, the human enzyme and the structurally similar enzyme from the yeast, $S.$ $cerevisiae$, cannot cleave the same substrate. However, the $E.$ $coli$ RNAase P can cleave a synthetic tRNA-related substrate that is also cleaved by the human RNAase P.

For bacterial RNAse P a half-turn of an RNA helix and a 3' proximal CCA sequence contain sufficient recognition elements to allow the reaction to proceed. Using these principles, any RNA sequence can be converted into a substrate for bacterial RNAase P by using an external guide sequence, having at its 5' terminus nucleotides complementary to the nucleotides 3' to the cleavage site in the RNA to be cleaved and at its 5' terminus the nucleotides NCCA (N is any nucleotide). The complementary nucleotides can include any number that allows hybridization to nucleotides 3' to the site to be cleaved. In some embodiments, the complementary nucleotides include at least fifteen nucleotides. In some embodiments the complementary nucleotides include a number of nucleotides sufficient to hybridize uniquely to the nucleotides 3' to the site to be cleaved. In some embodiments the complementary nucleotides have about fifteen nucleotides. It is not critical that all nucleotides be complementary, although the efficiency of the reaction will decrease as the degree of complementarity decreases. The rate of cleavage is dependent on the RNAase P and the solution structure of the hybrid substrate, which includes the targeted RNA and the presence of the 3'-NCCA in the hybrid substrate (where "N" is a purine).

EGS for promoting RNAase P-mediated cleavage of RNA have also been developed for use in eukaryotic systems as described by U.S. Pat. No. 5,624,824 to Yuan, et al., U.S. Pat. No. 6,610,478 to Takle, et al., WO 93/22434 to Yale University, WO 95/24489 to Yale University, and WO 96/21731 to Innovir Laboratories, Inc. Eukaryotic EGS molecules can be designed by adapting the basic structure of a pre-tRNA molecule (pre-tRNA$^{Tyr}$) and adding substrate recognition sequences, as described, for example, in WO 92/03566. For example, sequences complementary to the target sequences can be substituted for the sequences of the aminoacyl acceptor stem and the D stem. Such substituted sequences are referred to as guide arms. The guide arm corresponding to the aminoacyl acceptor stem is referred to as the A guide arm and the guide arm corresponding to the D stem is referred to as the D guide arm. The remaining sequences, which correspond to tRNA sequence and structural elements, are referred to as recognition sequences. The sequence of the guide arms are chosen to have regions specifically complementary to sequences in the target RNA immediately 3' of the desired cleavage site. The sequences of the guide arms are chosen such that the complementary regions of the targeted sequence are adjacent to each other but separated by a small unpaired region. The guide arms can be any length that results in a functional EGS molecule. In general, the 3'-terminal guide arm should be at least seven nucleotides long and have a region complementary to the target RNA molecule at least seven nucleotides long.

It has been discovered that, in addition to the guide arms, functional EGS molecules require only a structure corresponding to the T stem and loop of precursor tRNA having the sequence UUCG, which is the recognition sequence for eukaryotic RNase P. Thus, a functional EGS molecule requires only a T stem and loop having the sequence UUCG. The T stem and loop of an EGS molecule in eukaryotes can be any length or sequence that results in a functional EGS molecule, that is, an EGS molecule that mediates RNase P cleavage of a target RNA molecule in eukaryotes. For example, any tRNA T loop sequence including UUCG can be used. EGS molecules with loop lengths of 6, 7 and 8 nucleotides are functional. EGS molecules with limited sequence changes in the T loop, beyond the variations found in tRNA T loop sequences, also retain EGS function. The T stem can have any sequence which forms a stem structure. EGS molecules with stem lengths of 4, 5 and 6 base pairs are expected to be functional. It has also been discovered that the extra, or variable, loop, which appears between the D stem and T stem in tRNA molecules, is not required for EGS function. Accordingly, the EGS molecules described herein require only two guide arms, complementary to a target sequence, attached to the 5' and 3' ends of a T stem and loop recognition sequences. EGS molecules may also contain additional sequences and structures corresponding to those found in tRNA precursor molecules, such as a D loop or a 3'-terminal NCCA sequence. EGS molecules may also contain sequences at either or both distal ends that are not complementary to targeted sequences and are not related to tRNA structure. Such sequences are not considered to be a part of either the guide sequence or the recognition sequence.

The EGSs used to direct RNase P for targeted cleavage can resemble three-quarters of a tRNA molecule, however, studies have shown that shortened model substrates that retain some structural elements of a pre-tRNA (natural substrate of RNase P) can be recognized and hydrolyzed by RNase P or M1 RNA (the 377 nucleotide RNA subunit of $E.$ $coli$ RNase P). More specifically, deletion analysis of a tRNA substrate has shown that M1 RNA is capable of cleaving a "minimal model substrate" composed of the acceptor stem and T stem/loop, the 3' CCA sequence, and the 5' leader sequence of a pre-tRNA (Forster and Altman, $Science$, 249:783-6 (1990) and McClain, et al., $Science$, 238:527-30 (1987)).

In some embodiments, the EGS can be a M1GS RNA, such as those described in Lui and Altman, $Genes$ $Dev.$, 9(4):471-80 (1995). M1GS RNA is typically constructed by 3' extension of M1 RNA by a guide sequence that is an antisense sequence complementary to the target mRNA sequence and a recognition sequence containing an unpaired 3'-NCCA end as present in natural tRNA substrates (Kim and Liu, *Biochim Biophys Acta.,* 1769(11-12): 603-612 (2007)). This design is based on the idea that the guide sequence binds to its target mRNA and directs M1 RNA, which is in close proximity due to attachment to the guide sequence, to the site of cleavage. Accordingly, in some embodiments, the oligonucleotide also includes a M1 RNA sequence. The M1 RNA can be linked directly or indirectly, covalently or non-covalently to the EGS sequence.

Unless otherwise specified, RNAase P refers to the RNAase P in the cell in which the RNA to be cleaved is located, whether endogenous, added to the cell, or as used in vitro. Many of the techniques described herein are known to those skilled in the art, as are methods for making, and sources of, reagents. The teachings of any references cited herein with respect to methods and reagents are specifically incorporated herein, as well as for the purpose of demonstrating the scope and level of skill in the art.

It is not necessary to provide RNAase P activity if the cleavage is to occur intracellularly in the nucleus since all cells contain RNAase P in their nuclei. RNAase P must be supplied if cleavage is to occur in the cytoplasm. As used herein for ease of convenience, RNAase P refers to the ribonucleoprotein consisting of the eukaryotic analogues of the *E. coli* C5 protein and M1 RNA, regardless of source, whether isolated, produced by chemical synthesis or, in the case of the RNA, transcription from the gene, referred to herein as H1 RNA. The RNA subunit need not necessarily manifest catalytic activity in the absence of protein subunits in vitro.

EGS molecules can be readily screened for the ability to promote cleavage, by RNAse P, of target RNA using a suitable functional assay such as the one described in Yuan et al., *Proc. Natl. Acad. Sci.,* USA, 89:8006-8010 (1992).

1. Design of the EGS Sequence

Oligonucleotides that include an EGS sequence typically include an antisense sequence complementary to the target mRNA sequence and a recognition sequence including a 3' CCA sequence. The antisense sequence complementary to the target mRNA does not have to be 100% complementary to the target mRNA. For example, a mismatch of 3 nucleotides out of a 12 nucleotide antisense sequence had little effect on the success of the EGS sequence (McKinney J, *Proc. Natl. Acad. Sci. USA,* 98:6605-6610 (2001)) if the 3 nucleotides are not contiguous or are not located close to each other. In some embodiments, there can be two consecutive nucleotide differences between the ESG antisense sequence and the target mRNA. Accordingly, in some embodiments the antisense sequence of the EGS is 75%, 80%, 85%, 90%, 95%, 96%, 97%, 98%, 99%, 100% complementary to the target mRNA. It is believed that increasing complementarity increases the efficacy of the EGS. Accordingly, increasing complementarity can correlate with decreasing dose for some EGS sequences.

EGS sequences with as few as 5 nucleotides of complementarity to the mRNA target sequence can be effective for reducing or inhibiting expression of a gene, particularly if the complementary base pairing results in strong binding to the target region. Accordingly, in some embodiments the antisense sequence of the EGS can have 5, 6, 7, 8, 9, 10, 11, 12, 13, 14, 15, 16, 17, 18, 19, 20, 21, 22, 23 or more nucleotides complementary to the target mRNA. It is believed that EGS sequences including about 17 nucleotides complementary to the target mRNA sequence are more efficacious than EGS sequence with fewer than 17 nucleotides. Accordingly, having an EGS sequence including about 17 or more antisense nucleotides plus an ACCA recognition sequence at their 3' termini can be used at a lower dose than an EGS sequence that includes less than 17 antisense nucleotides directed to the same target mRNA sequence.

EGS can be used to target any mRNA of interest by including an antisense sequence complementary to the target mRNA sequence. Rational for design of EGS to target any mRNA sequence of interest are known in the art. See for example, Kim and Liu, *Biochim Biophys Acta.,* 1769(11-12): 603-612 (2007), which describes that careful selection of a target region is necessary due to RNA secondary structure and protein association can hamper the recognition and catalysis by M1GS RNA or RNase P. Accessibility of the target mRNAs can be mapped in vitro and in vivo, using numerous methods that are known in the art including, for example, techniques involving dimethyl sulfate (DMS) mapping as described in Trang, et al., *J. Mol. Biol.,* 25; 301(4):817-26 (2000) and Zhu, et al., *Proc Natl Acad Sci USA.,* 101(24):9073-8 (2004). Target site can also be identified using software programs that approximate secondary structures from sequence information (Mathews, et al., *Proc Natl Acad Sci USA.,* 101(19):7287-92 (2004), and Zuker, *Nucleic Acids Res.,* 31(13):3406-15 (2003)). Using this approach, some of the more thermodynamically stable regions in the target mRNA can be identified. Target sites buried in these regions would not be suitable as potential targets of ribozymes. Furthermore, if RNA-RNA interactions or RNA-protein interactions are known to be present at a sequence within the target mRNA, these interactions are predicted to reduce target accessibility.

The sequence of the target mRNA adjacent to the sequence targeted by the EGS can also be important for efficacy of the EGS. For example, for M1GS targeting, the nucleotides 3' and 5' adjacent to the site of cleavage are preferably a guanosine and a pyrimidine, respectively, Liu and Altman, *Nucleic Acids Res.,* 24(14):2690-6 (1996). For human RNase P targeting, preferably the mRNA includes a U at a location eight nucleotides downstream from the cleavage site (Yuan and Altman, *Science,* 263(5151):1269-73 (1994)). These sequence elements interact with the EGS to facilitate the formation of the mRNA-EGS complex into a tRNA-like structure can be needed for recognition and cleavage by the RNase P. Accordingly, in some embodiments EGSs used in combination with the CPP can be designed to specifically target a RNA molecule of choice.

2. Target Specific EGS Sequences

As discussed in more detail below, the compositions and methods are useful as antimicrobial agents and for use in treating microbial infections. Targeted RNA such as mRNA or viral RNA that can be inhibited by compositions and methods, including those expressed from essential microbial genes and antimicrobial resistance genes. Examples of essential microbial genes and antimicrobial resistance, as well as the EGS target sequence on the associated mRNA include those disclosed in the Examples. As discussed in more detail below, EGS can be composed of RNA nucleotides, DNA nucleotides, nucleotide analogs that have been chemically modified to improve stability, half-life, or specificity or affinity for a target sequence, relative to a DNA or RNA counterpart. For example, in a preferred embodiment, the EGS is a morpholino oligonucleotide. The EGS can be composed of cytosine, adenine, guanine, and uracil or thymine as the heterocyclic bases. Therefore, it is understood that in the morpholino nucleic acid sequences disclosed herein, "U" (uracil) can be substituted for "T" (thymine) and "T" (thymine) can be substituted for "U" (uracil).

Representative EGS target regions in the gyr genes in various microbes can include the sequence:
CGGTCAGGGTAAC (SEQ ID NO:4 *Escherichia coli*),
CGGTCAGGGCAAC (SEQ ID NO:5 *Acinetobacter*),
CGGTCACGGAAAC (SEQ ID NO:6 *Bacillus subtilis*),
TGGCCAGGGTAAC (SEQ ID NO:7 *Enterobacter cloacae*),
CGGCCACGGAAAC (SEQ ID NO:8 *Enterococcus faecalis*),
CGGCAGGGTAAC (SEQ ID NO:9 *Klebsiella pneumonia*),
CGGTCAGGGCAAC (SEQ ID NO:5 *Mycobacterium marinarum*),
CGGTCAGGGCAAC (SEQ ID NO:5 *Pseudomonas syringae*),
TGGTCAGGGTAAC (SEQ ID NO:12 *Salmonella enterica* ssp. *typhimurium*), or
TGGCCAAGGTAAC (SEQ ID NO:13 *Staphylococcus aureus*), or a sequence 90%, 95%, 96%, 97%, 98%, 99% or more identical to SEQ ID NO:4, 5, 6, 7, 8, 9, 12 or 13.

An example of an EGS sequence that can be used to target any of SEQ ID NO:4, 5, 6, 7, 8, 9, 12 or 13 can include the sequence GTTACCCTGACCGACCA (SEQ ID NO:14) or a sequence 90%, 95%, 96%, 97%, 98%, 99% or more identical to SEQ ID NO:14.

In some embodiments, an EGS target region in PfGyrA of various organisms can include the sequence:
CGGTCAGGGTAACTTCGGT$^{330}$ (SEQ ID NO:15 *E. coli*),
AGGTTATGGTAATTTTGGT$^{825}$ (SEQ ID NO:16 *P. falciparum*)
TGGATATGGTAATTTTGGG$^{870}$ (SEQ ID NO:17 *P. yoelli*),
CGGATATGGTAATTTTGGA$^{786}$ (SEQ ID NO:18 *P. berghei*),
TGATTATTATAATTTTGAG$^{6457}$ (SEQ ID NO:19 *H. sapiens*) or a sequence 90%, 95%, 96%, 97%, 98%, 99% or more identical to SEQ ID NO: 15, 16, 17, 18 or 19. Numbers to the right of each SEQ ID are the positions in the sequence of the gene of the last 3' nucleotide in this particular segment within each full-length gene sequence.

Representative EGS sequences that can be used to target PfGyrA can include
5'-GAAGUACGAAGGUUCGAAUCCUUC-CCCCUGACUGGU-3' (SEQ ID NO:20 Ecgyr f.l. EGS),
5'-GAAGUACGAGGUUCGAAUCCUC-CCCUGACUGGU-3' (SEQ ID NO:21 Ecgyr EGS)
5'-GAAAUACGAAGGUUCGAAUCCUUC-CCCAUAACUGGU-3' (SEQ ID NO:22 Plfgyr f.l. EGS)
5'-GAAAUACGAGGUUCGAAUCCUC-CCAUAACUGGU-3' (SEQ ID NO:23 Plfgyr EGS)
5'-GAAAUACGAGGUUCGUGCCCUC-CCAUAACUGGU-3' (SEQ ID NO:24 Plfgyr2 EGS)
5'-GAAAUACGAGGUUCGA-CCUC-CCAUAACUGGU-3 (SEQ ID NO:25 PlfgyrΔ2 bp EGS).

or a sequence 90%, 95%, 96%, 97%, 98%, 99% or more identical to SEQ ID NO:20, 21, 22, 23, 24, or 25.

Other Examples of EGS sequences useful in the disclosed compositions include:
CTGACTGAAATGCCTCACCA (SEQ ID NO:26-CAT or a sequence 90%, 95%, 96%, 97%, 98%, 99% or more identical to SEQ ID NO:26, which can be used to reduce expression of a chloramphenicol drug resistance gene product (cat).
GACCGCCGAGTCACCACCA (SEQ ID NO:27—Gyr241, or a sequence 90%, 95%, 96%, 97%, 98%, 99% or more identical to SEQ ID NO:27, which can be used to reduce expression of gyrase gene product.

GTTACCCTGACCGACCA (SEQ ID NO:14—Gyr 313, or a sequence 90%, 95%, 96%, 97%, 98%, 99% or more identical to SEQ ID NO:14, which can be used to reduce expression of a gyrase gene product.
ACCCTGACCGACCA (SEQ ID NO:28—Gyr 313-14, or a sequence 90%, 95%, 96%, 97%, 98%, 99% or more identical to SEQ ID NO:28, which can be used to reduce expression of a gyrase gene product.
CTGACCGACCA (SEQ ID NO:29—Gyr 313-11, or a sequence 90%, 95%, 96%, 97%, 98%, 99% or more identical to SEQ ID NO:29, which can be used to reduce expression of a gyrase gene product.
GGTTTGAGGGACACCA (SEQ ID NO:30—MMbla, or a sequence 90%, 95%, 96%, 97%, 98%, 99% or more identical to SEQ ID NO:30, which can be used to reduce expression of a penicillin drug resistance gene product (bla).
TAAGGGCGACACACCA (SEQ ID NO:31—ECbla, or a sequence 90%, 95%, 96%, 97%, 98%, 99% or more identical to SEQ ID NO:31, which can be used to reduce expression of a penicillin drug resistance gene product (bla). Other EGS target regions and EGS sequences that can used with the CPP to reduce expression of specific gene products are known in the art. See, for example, Shen, et al., *PNAS*, 106(20):8163-8168 (2009), which describes the design of EGS compounds using the methods described in Forster and Altman, *Science*, 249:783-786 (1990), Guerrier-Takada and Altman, *Methods Enzymol*, 313:442-456 (2000), and Lundblad, et al., *PNAS*, 105:2354-2357 (2008) to inactivate expression of the cat gene in *E. coli* and the gyrA and rnpA genes in *E. coli* and *S. typhimurium*, the first of which is a drug resistance gene, and the latter two of which are essential genes.

3. Scrambled EGS Sequences

In some embodiments, the EGS used in combination with the CPP can be a scrambled, random or otherwise non-specific sequence. As discussed in more detail in the Examples below, conjugates with scrambled sequences which were effective as controls with the PPMOs used in examples because they showed no decrease in viability of test strains under the conditions where gene-targeted PPMOs showed antimicrobial effects (Shen, et al., *Proc Natl Acad Sci USA*., 106:8163-8168 (2009)). However, scrambled sequences conjugated to the CPP had a significant effect on viability to bacterial cells (see Table 6 below). Scrambled sequences including as few as 5 nucleotides can have partial complementarity to various RNAs as judged by genomic searches in *E. coli*. Accordingly, it is believed that randomly generated EGS sequences conjugated to the CPP are also effective for inhibition of gene expression and reduced viability of transfected cells.

Examples of scrambled EGS sequences that can be effective to reduce the viability of a cell, for example a bacterial cell, when administered to the cell in combination with a CPP include, but are not limited to:
CTGTTCACTAGCTTGCAA (SEQ ID NO:32) SCR07 (full length)
CTAGC (SEQ ID NO:33) SCR5,
CACTAGCTT (SEQ ID NO:34) SCR9,
TTCACTAGCTTGC (SEQ ID NO:35) SCR13,
TTTTTTTTTTT (SEQ ID NO:36) T11,
CGGTGCGGGCCTCACCA (SEQ ID NO:37) lac,
or a sequence 90%, 95%, 96%, 97%, 98%, 99% or more identical to SEQ ID NO: 32, 33, 34, 35, 36, or 37 which can be used to reduce viability of microbes such as bacteria. As discussed in the Examples below, SEQ ID NO:37, which was designed to target lac mRNA, is effective to reduce viability of cells in both a wild type *E. coli* and a strain with a deletion in the lac gene indicating that gene specific targeting, itself, is not solely responsible for antimicrobial properties of the compounds.

4. Composition of the Oligonucleotides

The oligonucleotides include a sequence of eleven or more nucleotides. The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In preferred embodiments, the oligonucleotides are composed of nucleotide analogs that have been chemically modified to improve stability, half-life, or specificity or affinity for a target sequence, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge. Modifications should not prevent, and preferably enhance, the ability of the oligonucleotides to enter a cell and carry out a function such inhibition of gene expression as discussed above.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

As discussed in more detail below, in one preferred embodiment, the oligonucleotide is a morpholino oligonucleotide.

Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or deoxyribose and also forms a bridge with the i−1 phosphate in the purine strand of the duplex.

In a preferred embodiment, the oligonucleotide is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above. Especially preferred is a substantially uncharged phosphorodiamidate-linked morpholino oligomer, also referred to herein as a PMO.

Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527,675, 5,623,049, 5,714,331, 5,736,336, 5,773,571 and 5,786,571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. For example, lysine and arginine residues can be added to a bis-PNA linker or can be added to the carboxy or the N-terminus of a PNA strand. Oligonucleotides may further be modified to be end capped to prevent degradation using a 3' propylamine group. Procedures for 3' or 5' capping oligonucleotides are well known in the art.

C. Cell Targeting Moieties

In some embodiments, the CPP or oligonucleotides include a cell targeting moiety. Examples of moieties which may be linked or unlinked to the compounds include, for example, targeting moieties which provide for the delivery of molecules to specific cells, e.g., antibodies to bacterial or parasitic protein as well as receptor and ligands expressed on the preferred cell type.

D. Additional Prophylactic or Therapeutic Agents

The compositions including the CPP in combination with, or conjugated to an oligonucleotide can be used alone or in combination with other prophylactic or therapeutic agents. As used herein, two agents are said to be used in combination when the two agents are co-administered, or when the two agents are administered in a fashion so that both agents are present within the cell or serum simultaneously. In preferred antimicrobial compositions or compositions for treating microbial infections, the composition can be administered in combination with a conventional antimicrobial drug.

Antimicrobial drugs either kill microbes (microbiocidal) or prevent the growth of microbes (microbiostatic). Antimicrobial agents can be classified as antibacterial, antifungal, antiviral, or antiparasitic depending on the type of microbe the drug targets. Examples of antibiotics include, but are not limited to, penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftrizoxime, ceftriaxone, and cefoperazone. Examples of antimicrobial/antiseptics include, but are not limited to, silver sulfadiazine, chlorhexidine, peracetic acid, sodium hypochlorite, triclosan, phenols, phenolic compounds, iodophor compounds, quaternary ammonium compounds, chlorine compounds, heparin and combinations thereof. Examples of anti-viral agents include, but are not limited to, alpha-methyl-1-adamantanemethylamine, hydroxy-ethoxymethylguanine, adamantanamine, 5-iodo-2'-deoxyuridine, trifluorothymidine, interferon, and adenine arabinoside.

In a preferred embodiment, the composition includes a CPP in combination with, or conjugated to an antisense oligonucleotide such as an EGS which targets an antimicrobial resistance gene, and a dose of the drug to which the antimicrobial resistance gene imparts resistance to the microorganism. For example, in some embodiments, the compositions include CPP in combination with a morpholino oligonucleotide including an EGS sequence that targets the drug resistance gene cat, in combination with a dose of chloramphenicol. In some embodiments, the compositions include CPP in combination with a morpholino oligonucleotide including an EGS sequence that targets the drug resistance gene bla, in combination with a dose of penicillin.

Figure 2:
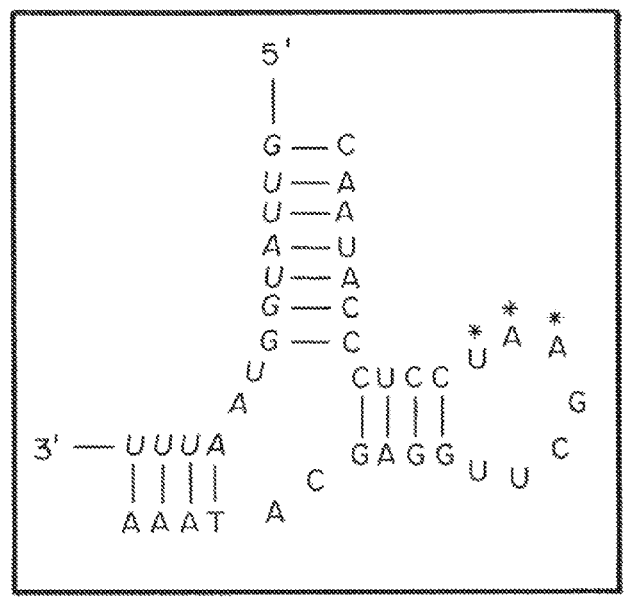
FIG. 2 is a schematic of EGS-mRNA binding. Plfgyr-EGS (SEQ ID NO:47) is shown binding to a fragment of Plfgyr mRNA (in italics (SEQ ID NO:48)). Nucleotides in the Plfgyr-EGS (SEQ ID NO:47) involved in hydrogen bonding with the mRNA of Plfgyr (SEQ ID NO:48) are in bold; stem-loop for RNase P recognition in normal font; A*A*U* as shown in Plfgyr-EGS (SEQ ID NO:47) are replaced with TGC respectively in Plfgyr2-EGS (SEQ ID NO:54).

In some embodiments, the composition includes a CPP in combination with, or conjugated to an antisense oligonucleotide such as an EGS which targets an essential gene in a microorganism and a dose of an antimicrobial drug. For example, the gyrase A gene from *E. coli* harbors a short sequence, which is highly conserved across many bacteria, and has successfully been targeted for RNase P-mediated degradation. This sequence is also partially conserved in the gyrA gene of *P. falciparum*, which should play an essential function in parasite replication (FIG. 2). Accordingly, in some embodiments, the compositions include CPP in combination with a morpholino oligonucleotide including an EGS sequence that targets the gyrA gene of *P. falciparum* in combination with a dose of an antimalarial drug such as chloroquine or hydroxychloroquine.

E. Formulations

The disclosed compositions including CPP and oligonucleotides can be employed for therapeutic uses in combination with a suitable pharmaceutical carrier. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids.

It is understood by one of ordinary skill in the art that nucleotides administered in vivo are taken up and distributed to cells and tissues (Huang, et al., *FEBS Lett.*, 558(1-3):69-73 (2004)). For example, Nyce, et al. have shown that antisense oligodeoxynucleotides (ODNs) when inhaled bind to endogenous surfactant (a lipid produced by lung cells) and are taken up by lung cells without a need for additional carrier lipids (Nyce, et al., *Nature*, 385:721-725 (1997)). Small nucleic acids are readily taken up into T24 bladder carcinoma tissue culture cells (Ma, et al., *Antisense Nucleic*

*Acid Drug Dev.*, 8:415-426 (1998)). However, co-administration of an oligonucleotide with the CPP, or conjugation of the oligonucleotide to the CPP can increase delivery, activity or combination thereof of the oligonucleotide in the cell.

The disclosed compositions including CPP and oligonucleotide may be in a formulation for administration topically, locally or systemically in a suitable pharmaceutical carrier. Remington, *The Science and Practice of Pharmacy*, 22nd edition, (Edited by Allen, Loyd V., Jr), Pharmaceutical Press (2012), discloses typical carriers and methods of preparation. The compound may also be encapsulated in suitable biocompatible microcapsules, microparticles, nanoparticles, or microspheres formed of biodegradable or non-biodegradable polymers or proteins or liposomes for targeting to cells. Such systems are well known to those skilled in the art and may be optimized for use with the appropriate nucleic acid.

For example, in general, the disclosed compositions can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polyesters, polysaccharides, polyanhydrides, polyorthoesters, polyhydroxides and proteins and peptides.

Liposomes can be produced by standard methods such as those reported by Kim, et al., Biochim. Biophys. Acta, 728, 339-348 (1983); Liu, D., et al., Biochim. Biophys. Acta, 1104, 95-101 (1992); and Lee, et al., Biochim. Biophys. Acta., 1103, 185-197 (1992); Wang, et al., Biochem., 28, 9508-9514 (1989)), incorporated herein by reference. The disclosed compositions can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the composition to be encapsulated, and the resulting hydrated lipid vesicles or liposomes encapsulating the material can then be washed by centrifugation and can be filtered and stored at 4° C. This method has been used to deliver nucleic acid molecules to the nucleus and cytoplasm of cells of the MOLT-3 leukemia cell line (Thierry, A. R. and Dritschilo, A., Nucl. Acids Res., 20: 5691-5698 (1992)). Alternatively the disclosed compositions can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner, P. L. et al., Proc. Natl. Acad. Sci. USA, 84: 7413-7417 (1987); Felgner, P. L., Advanced Drug Delivery Reviews, 5: 163-187 (1990); Clarenc, J. P. et al., Anti-Cancer Drug Design, 8: 81-94 (1993). Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl-] N,N,N-triethylammonium ("DOTMA," see Felgner, P. L. et al., Proc. Natl. Acad. Sci. USA, 84, 7413-7417 (1987); Felgner, P. L. et al., Nature, 337, 387-388 (1989); Felgner, P. L., Advanced Drug Delivery Reviews, 5, 163-187 (1990)).

Nucleic acid can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., Science, 261: 209-211 (1993)).

Liposomes containing either EGS molecules or DNA encoding these molecules, can be administered systemically, for example, by intravenous or intraperitoneal or pulmonary administration, in an amount effective for delivery of the disclosed compositions to targeted cells. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect.

Compositions including various polymers such as the polylactic acid and polyglycolic acid copolymers, polyethylene, and polyorthoesters and the disclosed compositions can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the therapeutic anti-hepatitis EGS compositions to the immediate area of the implant.

Various methods for nucleic acid delivery are described, for example, in Sambrook and Russell, Molecular Cloning: A Laboratory Manual, 3rd edition (2001); Current Protocols In Molecular Biology [(F. M. Ausubel, et al. eds., (1987)]; Plant Breeding: Principles and Prospects (Plant Breeding, Vol 1) M. D. Hayward, N. O. Bosemark, I. Romagosa; Chapman & Hall, (1993); Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)]. Such nucleic acid delivery systems include the desired nucleic acid, by way of example and not by limitation, in either "naked" form as a "naked" nucleic acid, or formulated in a vehicle suitable for delivery, such as in a complex with a cationic molecule or a liposome forming lipid, or as a component of a vector, or a component of a pharmaceutical composition, as discussed above. The nucleic acid delivery system can be provided to the cell either directly, such as by contacting it with the cell, or indirectly, such as through the action of any biological process. The nucleic acid delivery system can be provided to the cell by endocytosis, receptor targeting, coupling with native or synthetic cell membrane fragments, physical means such as electroporation, combining the nucleic acid delivery system with a polymeric carrier such as a controlled release film or nanoparticle or microparticle, using a vector, injecting the nucleic acid delivery system into a tissue or fluid surrounding the cell, simple diffusion of the nucleic acid delivery system across the cell membrane, or by any active or passive transport mechanism across the cell membrane. Additionally, the nucleic acid delivery system can be provided to the cell using techniques such as antibody-related targeting and antibody-mediated immobilization of a viral vector.

Formulations for topical administration may include ointments, lotions, creams, gels, drops, sprays, liquids and powders. Conventional pharmaceutical carriers can be used as desired. Formulations suitable for parenteral administration, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, optionally with an added preservative.

The compositions may take such forms as sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, and electrolyte replenishers (such as those based on Ringer's dextrose). Preservatives and other additives may also be present such as, for example, antimicrobials, antioxidants, chelating agents and inert gases.

In addition, sterile, fixed oils are conventionally employed as a solvent or suspending medium. For this purpose any bland fixed oil including synthetic mono- or di-glycerides may be employed. In addition, fatty acids such as oleic acid may be used in the preparation of injectables. Carrier formulation can be found in Remington's (supra).

The CPP and oligonucleotides alone or in combination with other suitable components, can also be made into aerosol formulations (i.e., they can be "nebulized") to be administered via inhalation. For pulmonary administration, formulations can be administered using a metered dose inhaler ("MDI"), a nebulizer, an aerosolizer, or a dry powder inhaler. Suitable devices are commercially available and described in the literature.

Inhaled aerosols have been used for the treatment of local lung disorders including asthma and cystic fibrosis (Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)). Considerable attention has been devoted to the design of therapeutic aerosol inhalers to improve the efficiency of inhalation therapies. Timsina et. al., Int. J. Pharm., 101: 1-13 (1995); and Tansey, I. P., Spray Technol. Market, 4: 26-29 (1994).

The formulation may be administered alone or in any appropriate pharmaceutical carrier for administration to the respiratory system. Delivery is achieved by one of several methods. For example, the patient can mix a dried powder of CPP-oligonucleotide with solvent and then nebulize it. It may be more appropriate to use a pre-nebulized solution, regulating the dosage administered and avoiding possible loss of suspension. After nebulization, it may be possible to pressurize the aerosol and have it administered through a metered dose inhaler (MDI). Nebulizers create a fine mist from a solution or suspension, which is inhaled by the patient. Dry powders are particularly preferred.

Systemic administration can also be by transmucosal means. For transmucosal administration, penetrants appropriate to the barrier to be permeated are used in the formulation. Such penetrants are generally known in the art, and include, for example, for transmucosal administration, detergents, bile salts, and fusidic acid derivatives.

In one embodiment, the oligonucleotides are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., *Bioorg. Med. Chem. Lett.,* 14(19):4975-4977 (2004)) and in vivo (Soutschek, et al., *Nature,* 432(7014): 173-178 (2004)).

In addition, it has been shown that binding of steroid conjugated oligonucleotides to different lipoproteins in the bloodstream, such as LDL, protect integrity and facilitate biodistribution (Rump, et al., *Biochem. Pharmacol.,* 59(11): 1407-1416 (2000)). Other groups that can be attached or conjugated to the compound described above to increase cellular uptake, include acridine derivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties; nucleases such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines U.S. Pat. No. 6,919,208 to Levy, et al., also describes methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

F. Dosages and Effective Amounts

The disclosed compositions typically include an effective amount of CPP to increase the delivery of a cargo, such as an oligonucleotide, into a cell relative to a control. In some embodiments, the CPP can be administered alone in an effective amount to reduce viability of microorganism compared to a control, such as untreated cells. In some embodiments, a composition including a CPP and an antisense oligonucleotide are administered together in an effective amount to reduce expression of a gene product relative to a control. A control can be untreated cells, or cells treated with the oligonucleotide in the absence of the CPP. As discussed in the Examples below, the CPP conjugated to a morpholino oligonucleotide EGS reduced the viability of bacteria compared to alternative CPP conjugated to the same morpholino oligonucleotide EGS. Accordingly, in some embodiments, a control can be cells treated with an alternative CPP conjugated to a morpholino oligonucleotide EGS.

Dosages and desired concentrations of the CPP and oligonucleotides in pharmaceutical compositions will vary depending on the particular use envisioned. The determination of the appropriate dosage or route of administration is within the skill of one in the art. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

It has been shown that small nuclease resistant EGS are readily taken up into T24 bladder carcinoma tissue culture cells with carrier lipids at a concentration of 1 μM EGS and 10 μM lipid transfection reagents Lipofectin or Lipofectase (Ma, eta 1., Antisense Nucleic Acid Drug Dev. 8:415-426 (1998). Uptake of these EGS was noted in both cytoplasm and nuclei of nearly every cell using 5'-fluoresceinated EGS detected by confocal microscopy. Significant decreases in targeted gene expression were demonstrated in this model in the absence of observed toxicity. These studies demonstrated that modified EGS can be used for targeted gene therapy of human diseases. The formulations contain an effective amount of EGS to reach a final EGS concentration of 1 micromolar or less in pulmonary extracellular fluid (approximately 10-15 cc) to decrease levels of targeted mRNA for days or weeks following intranasal administration. For example, this range of EGS concentration can be achieved by intranasal instillation of 0.01 micromoles of EGS. Like conventional asthma medications it is anticipated that EGS can be shipped through the mail and stored at room temperature, but unlike conventional therapy it is expected that a single dose will have therapeutic effects for days or even weeks due to long term effects upon target protein synthesis (Ma, et al., Nat. Biotechnol. 18(1):58-61 (2000) and Ma, et al., Antisense Nucleic Acid Drug Dev. 8:415-426 (1998).

In one report, the concentration of EGS was determined to approximate 1 micromolar in pulmonary fluids, which was optimal for gene targeting in vitro (Ma, et al., Nat. Biotechnol. 18(1):58-61 (2000)).

In another report, MCMV-infected mice were orally treated with *Salmonella* carrying EGS expression cassettes, viral gene expression and growth in various organs of these animals were reduced and animal survival improved (Jiang, et al., *PNAS,* 109(32):13070-13075 (2012). All mice infected with SL201 strain ($1\times10^9$ cfu/mouse) remained alive at 80 d post inoculation. In contrast, mice inoculated with a much lower dose of ST14028s strain ($1\times10^3$ cfu/mouse) and SL7207 strain ($5\times10^5$ cfu/mouse) died within 7 and 15 d post inoculation, respectively.

Toxicity and therapeutic efficacy formulations can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any EGS used in the method of the invention, the therapeutically effective dose can be estimated initially from cell culture assays. A dose may be formulated in animal models to achieve a circulating plasma concentration range of the EGS that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The Examples below show that the compositions can be up to 100 fold more efficacious than previously reported compositions, and be used at concentration at least 10-fold lower than previously used (Shen, et al., *Proc. Natl. Acad. Sci. USA.,* 106:8163-8168 (2009). Accordingly, in some embodiments, the dosage of the CPP-EGS is lower than the dosage of previously report EGS or other antisense technologies.

III. Methods of Use

The compositions are typically used to reduce gene expression in cell by contacting the composition with the cell. The contacting can occur in vitro, in vivo, or ex vivo. For example, as discussed in more detail below, in some embodiments, the compositions can be administered to a subject such as a human or used to coat or impregnate a device or instrument used on or implanted into a subject

A. Diseases to be Treated

The compositions including a CPP typically include an oligonucleotide, which can be administered separately or conjugated to the CPP. In preferred embodiments, the oligonucleotide is an inhibitory nucleic acid, for example an EGS, which inhibits gene expression. Compositions including a CPP and inhibitory oligonucleotide can be used to treat any disease for which inhibition, reduction, or elimination of a gene product is desired. In a preferred embodiment, the compositions are used as an antimicrobial agent. The compositions can be used to non-specifically, or specifically reduce microbe viability. For example, in some embodiments the CPP is used in combination with an inhibitory oligonucleotide such as an EGS to reduce gene expression of an essential gene or drug resistance gene in a microbe such as bacteria, virus, fungus, protist, protozoa, and other parasites.

Viral infections that can be treated using the disclosed therapies include, but are not limited to, infections caused by Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxyiridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae.

Bacterial infections that can be treated using the disclosed therapies include, but are not limited to, infections cause by

*Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

Parasitic infections that can be treated using the disclosed therapies included infections caused by *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.*

In some embodiments, the infection treated using the disclosed compositions are caused by antibiotic resistant microorganisms such as antibiotic resistant *Staphylococcus aureus, Streptococcus, Enterococcus, Pseudomonas aeruginosa, Clostridium difficile, Salmonella, E. coli, Acinetobacter baumannii,* or *Mycobacterium tuberculosis.*

As discussed above, the disclosed compositions can be designed to target an essential gene in the microorganism. For example, the compositions can be designed to target genes important for cell wall synthesis, DNA replication, RNA transcription, folate synthesis or protein synthesis. In some embodiments, the target can be a gene important for infection or virulence of the microorganism. For example, the compositions can be designed to target gene important for toxin function, toxin delivery, regulation of virulence expression, and cell adhersion was discussed in Clatworthy, et al., *Nature Chemical Biology,* 3:541-548 (2007).

In some embodiments, the target gene is an antibiotic or antimicrobial resistance gene. Antibiotic resistance genes are known in the art, see for example, the Antibiotic Resistance Genes Database (ardb.cbcb.umd.edu) and U.S. Pat. No. 5,976,874 to Yale University.

In some embodiments, the region of the microbial gene that is targeted by the inhibitory oligonucleotide has little or no sequence identity to a gene in the host or subject to which the composition is being administered. Accordingly, in some embodiments, the microbial gene targeted by the inhibitory oligonucleotide does not have homology in the host or subject being treated.

In some embodiments, the compositions are designed to treat a number of microorganisms at one time be designing the oligonucleotide to target a gene that has high homology or identity across two or more organisms, for example the GyrA gene. In some embodiments, the compositions are designed to be selective target a specific microorganism by targeting a gene unique or specific to the organism, or with low homology or sequence identity in other organisms. In some embodiments, the EGS is designed be recognized by the RNase P of the target species, but not the host species. For example, in some embodiments, the EGS can be recognized by bacterial RNase P, but not a eukaryotic RNase P. In some embodiments, the EGS can be recognized by the host species' RNase P.

B. Methods of In Vivo Administration

The formulations may be administered by any means known in the art including, but not limited to oral or parenteral routes, including intravenous, intramuscular, intraperitoneal, subcutaneous, transdermal, and airway (aerosol) administration. In some embodiments, the formulations are administered via inhalation or nasal application to the lung. The formulations are administered to a patient in need of treatment or prophylaxis. The formulations can be administered to animals or humans.

The route of administration can be determined depending subject or patient specific factors such as the disease to be treated, whether local or systemic treatment is desired, and on the area to be treated. Administration may be topically, orally, by inhalation, or parenterally. The formulation may be administered once daily, or the composition may be administered as two, three, four, five, six or more sub-doses at appropriate intervals throughout the day. In that case, the composition contained in each sub-dose can be correspondingly smaller in order to achieve the total daily dosage. The dosage unit can also be compounded for delivery over several days, e.g., using a conventional sustained release formulation which provides sustained release of the composition over a several day period. Sustained release formulations are well known in the art. In this embodiment, the dosage unit contains a corresponding multiple of the daily dose.

One of skill in the art will appreciate that certain factors may influence the dosage and timing required to effectively treat a subject, including but not limited to the severity of the disease or disorder, previous treatments, the general health and/or age of the subject, and other diseases present. Treatment of a subject with a therapeutically effective amount of a composition can include a single treatment or a series of treatments. Estimates of effective dosages and in vivo half-lives for the individual EGSs can be made using conventional methodologies or on the basis of in vivo testing using an appropriate animal model, as described elsewhere herein.

The efficacy of treatment can be monitored by measuring the amount of the target gene mRNA (e.g. using real time PCR) or the amount of polypeptide encoded by the target gene mRNA (Western blot analysis). The efficacy of treatment can also be determined by methods known to one of ordinary skill in the art with respect to the effect the CPP, the oligonucleotide, or a combination thereof has on the symptoms of the disease to be treated. For example, in some embodiments, the efficacy of the treatment can be measure by a reduction in microbial load or viability as discussed in the Examples below.

It is expected that CPP compositions containing specific EGS will have less non-specific effects and less non-specific inflammatory effects than comparable gene targeting with RNAi or conventional antisense DNA. The reason for this expectations is that 1) EGS are significantly smaller than comparable RNAi (32 modified RNA nucleotides for typical nuclease resistant EGS versus. 21-23 nucleotide double strand=42-46 total nucleotide RNAi), 2) EGS have significantly less double stranded RNA than RNAi, which is capable of triggering toll-3 innate immune receptors 3) EGS do not have DNA CpG motifs present in DNA based anti-sense, which is capable of triggering toll-9 innate immune receptors 4) EGS are based on activation of RNAse P, a housekeeping enzyme not induced or regulating the host anti-viral response in contrast to RNAi activated RISC and double strand DNA activated RNAse H. RISC and RNAse H are both members of a common recombinase pathway regulated by viral and other inflammatory signals.

Gene chip whole genome screens are readily available which can be used to examine off targeting effects at the transcriptional level of virtually the entire transcriptosome (more than 20,000 expressed sequence tags and controls, Affymetrix, Santa Clara, Calif.).

Stability and quantitative tissue distribution of the disclosed compositions can be assessed by sequence analysis of oligonucleotides recovered from tissues using PCR with primers specific for the 5' and 3' termini of the oligonucleotide and Northern blotting using oligonucleotide sequences. Evidence of integration of oligonucleotide into the host genome can be detected using PCR of genomic DNA with one primer specific for the oligonucleotide and a second for host repetitive sequences and southern blotting of whole chromosomes separated by pulsed field electrophoresis and probed with labeled oligonucleotide.

C. Methods of Reducing Institutional or Iatrogenic Infections

Hospital acquired infections are frequent complications following surgical procedures, particularly when intravascular devices are inserted, and are commonly associated with skin microorganisms, for example, *Staphylococcus epidermidis*. Several factors contribute to establishment of the infection, for example, inadequate skin disinfection prior to skin penetration and the emergence of resistant microorganisms within the clinical setting, often due to the wide use of antimicrobial agents including antibiotics, antiseptics and other biocides.

Microorganisms may exist as microcolonies within the skin or as biofilms in situ on intravascular devices, for example on the surface of a catheter, and are therefore more resistant to higher concentrations of antimicrobials compared to microorganisms in suspension. Furthermore, many of the strong antiseptics are toxic and cannot be administered directly to a subject, or remain as a residue on the surface of medical instrument or device that may introduced into a subject.

The disclosed compositions can be used to prevent or reduce institutional infections. For example, the compositions can be coated onto a surgical device or medical device to prevent, reduce, decrease, or inhibit the appearance of institutional or opportunistic infections that are acquired during or as a result of a surgical procedure or a hospital visit. For example, the compositions can be implanted in or coated onto surgical or medical devices before or during introduction of the device into the patient. The composition can be designed for sustained or controlled release following implantation. Preferred examples include catheters, and vascular valves, stents or grafts, or other devices that are permanent, semi-permanent, or temporarily inserted into the subject.

The compounds can also be used in a wound dressing. For example, the compositions can be applied to damaged, diseased, or burned tissue, to enhance healing or reduce or prevent infection. In preferred embodiments, the compositions are applied to, incorporated into, or coated onto wound or burn healing dressings or into sutures. In a particularly preferred embodiment, these are delivered with dressings or treatments for non-healing chronic wounds such as decubitus or diabetic ulcers.

IV. Method of Functional Analysis

The disclosed compositions including a CPP and an inhibitory nucleic acid can be used for functional gene screening. Methods of functional gene screening using antisense technology have been used to characterize the function of the genes and are well known in the art. See, for example, U.S. Published Applications 2011/0172107 and 2005/0196862, Yonekura, et al., *NAR*, 27(13):2591-2600 (1999), and Flatschart and Sogayar *Braz. J. Med. Biol. Res.*, 32(7) 867-875 (1999). The disclosed compositions offer several advantages over traditional antisense screening. For example, the CPP facilitates entry of the inhibitory nucleic acid, such as an EGS, into the cell. Accordingly, the compositions can be introduced without the presence of additional transfection reagents or equipment such as liposomes or electroporation. Additionally, as discussed above, the compositions can include a CPP in combination with EGS. In some embodiments the EGS is conjugated to the CPP. In some organisms such as *P. falciparum*, RNA based antisense methods are ineffective. Therefore the use of CPP in combination with EGS can be used for functional genomic screening in organisms where screening is not possible using traditional RNA-based antisense reagents.

Generally, cells are contacted with the disclosed compositions including a CPP and an inhibitory nucleic acid, such as an EGS, and monitored for a phenotype. The methods can be used to identify essential genes. For example, reduced viability of a cell when contacted with the CPP and an inhibitory nucleic acid, such as an EGS, is indicative that the gene targeted by the inhibitory nucleic acid is an essential gene. The methods can also be used to identify drug resistance genes. For example, in some embodiments the cells are contacted with a CPP and an inhibitory nucleic acid in combination with a drug or therapeutic agent. Increased effectiveness or efficacy of the drug in the presence of the CPP and inhibitory nucleic acid is indicative that the gene targeted by the inhibitory nucleic acid imparts resistance to the drug or therapeutic agent.

The present invention will be further understood by reference to the following non-limiting examples.

EXAMPLES

Example 1

Basic Peptide-Morpholino Oligonucleotide Conjugates Localize within Bacterial Cells Materials and Methods
Bacterial Strains

*E. coli* SM105 and *E. coli* CAG5050 were obtained from the *E. coli* Culture Center at Yale University. *E. coli* BW was grown from the Altman lab collection. *Pseudomonas syringae*, grown at room temperature in trypsin soy broth (TSB), *Enterobacter cloacae* M322 and *Klebsiella pneumoniae*, grown in LB broth at 37° C., were obtained from John Wertz, Yale University. The following strains were obtained from the American Type Culture Collection: *Streptococcus salivarius, Enterococcus faecalis* and *Mycobacterium marinum*. *Acinetobacter* ADP1 was a gift from Dr. D. Parke, Yale University and was grown in TSB at 37° C. *E. faecalis* was grown in brain heart infusion (BHI) at 37° C. as was *S. salivarius*. *Staphylococcus aureus* RN4220 was a gift from Dr. A. L. Cheung, Dartmouth College and was grown in TSB at 37° C. *Bacillus subtilis* W168 was obtained from the *B. subtilis* Stock Center, Columbus, Ohio.

Synthesis and Column Purification of a Conjugated Peptide Phosphoroamidate Morpholino Oligonucleotide A cell-penetrating peptide (CPP), derived from human T cells (Choi, et al., *Proc Nat Acad Sci USA* 107:18575-18580 (2010)) was synthesized via solid-phase chemistry at the Keck Biotechnology Resource Laboratory of Yale University, and a phosphorodiamidate morpholino oligomer (PMO) with an appropriate base sequence was purchased from Gene Tools, LLC. The original basic polypeptide used, AB1, had an additional Cys residue at its C terminus.

Subsequently, as noted below, another basic polypeptide, AB2, was used that lacked the Cys residue at its C terminus. This polypeptide was made by the Keck facility at Yale University or Biopeptides, Inc. Reagents used for chemical synthesis were purchased from Sigma-Aldrich and were used without further purification. CPP conjugated PMO was synthesized by the Lebleu method Abes et al., *J Control Release* 116:304-313 (2006). The peptide was covalently bound to a primary amine at the 3' end of the PMO. In all the experiments in this report, deionized water was used.

To a solution of peptide acid (1.25 mg or lower) in 1-methyl-2-pyrrolidine (NMP, 0.5 mL) at room temperature were added 0-(benzotriazole-1-yl)-N,N,N',N'-tetramethyl-uronium hexafluoro phosphate (HBTU, 0.5 mg), N,N diisopropylethylamine (DIEA, 2 drops from a 20G1½ inch needle and a 1 mL Norm-Ject syringe), and 1-hydroxybenzotriazole (HOBt, 0.3 mg). The mixture was stirred at room temperature for 10 min, and a solution of a morpholino oligonucleotide (3.1 mg or lower) dissolved in DMSO (0.5 mL) was added to the mixture. The reaction mixture was stirred at 40° C. for 3 hours, cooled to 0° C. and diluted with $H_2O$ (5 mL).

The synthesized samples were diluted to a final volume between 10 and 15 mL and loaded onto a 30 mL CM-Sepharose column pre-washed with $H_2O$. The column was washed with $H_2O$ (100 mL) to remove unconjugated reactants and other mixtures and then the conjugate was eluted with 2M guanidine-HCl (50 mL). One or two mL fractions were collected. A NanoDrop ND-1000 Spectrophotometer (NanoDrop Technologies)) was used to read the $OD_{260}$ of each fraction and fractions were run on a standard 15% (w/v) polyacrylamide SDS-Laemmli gel to determine which fraction contains the conjugate. The conjugate came off in the fractions just after the $OD_{260}$ peak and the synthesis is diagramed briefly in FIG. 1.

The fractions with the conjugate were then run over a Supel-Select HLB SPE column (6 mL, 200 mg; Supelco) to remove guanidine and to concentrate the material. The column was prepared by washing with methanol (4 mL) followed by $H_2O$ (6 mL). The fractions with the conjugate were pooled, diluted 1:1 with $H_2O$, and loaded onto the column. The column was washed with $H_2O$ (12 mL) to remove salts and the conjugate was eluted with 50% (v/v) acetonitrile (6 mL). The first four eluted samples were collected in 0.5 mL fractions and the latter four were 1 mL. These fractions were then lyophilized in a Speedvac (Savant) concentrator. Purified conjugate fractions were resuspended in $H_2O$ and a Nanodrop Spectrophotometer was used to read the $OD_{260}$ of each fraction and concentrations were determined. The peak of purified conjugate was in fractions two and three.

Calculation of concentration of conjugate in $H_2O$ or in solutions of low molarity was achieved by measuring the optical absorbance at 260 nm in water of the PMO after that solution had been made by weighing out a standard amount from the dry material supplied by the manufacturer. The optical absorbance of conjugate was calculated using the PMO standard that was weighed out since the absorbance of the basic peptide and other chemicals in the conjugation mixture did not show high values at 260 nm. Storage of the conjugates in $H_2O$ solutions at 4° C. kept their original biological activity for several months.

Fluorescein labeled conjugates were made by covalently linking a morpholino oligonucleotide to a fluorescein labeled basic polypeptide made by the Keck synthesis facility at Yale University. The fluorescein was linked to the N-terminus of the polypeptide. The procedure for conjugation was the same as the one used for unlabeled conjugates.

Fluorescence of Conjugates in Bacteria

Three hundred µl of a 1:500 dilution of the overnight culture of *E. coli* were incubated with 1 µM of FL-AB2-gyr241 or water (negative control). As a positive control 10 µM of the tagged PPMO conjugate (PPMO-CAT-FL) was used. The cells were incubated with the respective conjugate for 3 h at 37° C. in a shaking incubator. The cells were then washed with PBS solution three times, harvested by centrifugation at 9000 g and the pellet was resuspended in 5 µL 1×M9. The cells were placed on agar coated slides (1% (w/v) agarose in 1×M9, 0.2% (v/v) glycerol) and covered with a glass coverslip, and immediately viewed under either a Nikon 80 I equipped with 100× phase contrast objective and a Hamamatsu Orca II ER camera or a Nikon Eclipse Ti microscope equipped with a 100× phase contrast objective and a Hamamatsu Orca ER camera. The images were analyzed using Metamorph. The same procedure was used for cells other than *E. coli*.

Assays of Effectiveness of Conjugates In Vivo and the Cleavage of Various RNAs In Vitro The methods described in Shen et al. (Shen et al., *Proc Natl Acad Sci USA* 106:8163-8168 (2009)) were used with the following modifications. Briefly, growing cultures that were diluted from overnight or stock cultures to a concentration of $10^4$ cells/mL, were mixed directly with the conjugate in liquid medium and the cells were incubated for another 4 h or 6 h as listed and assayed for phenotype. Unless noted otherwise in Materials and Methods, cells had been suspended in 50 µL after overnight growth in LB broth in 1.5 mL Eppendorf tubes and shaken with incubation for times given in table legends. One exception to this procedure is the growth of *Mycobacterium marinum*. In this case, cells were suspended in Middlebrook 7H9 medium with the ADC supplement (Difco) and grown at 30° C. in the dark for the appropriate time. *M. marinum* cells were plated on agar Middlebrook TH10 plates with the OADC supplement. *P. syringae*, was grown, as noted, at room temperature.

Results

Synthesis of New Conjugate

The peptide was covalently bound to a primary amine at the 3' end of the PMO (FIG. 1). No difference in biological activity between linkage at the 5' or 3' ends of the PMO was previously shown with other peptides (Shen et al., *Proc Natl Acad Sci USA* 106:8163-8168 (2009)). Several deletion versions of the peptide reported here (11, 14, 15 and 19 residues; Table 1) were linked to CAT or gyr PMOs but they had no biological effect at all. Some PMOs had different numbers of nt compared to a full-length conjugate and these are indicated by the last numbers in the name of the conjugate (Table 1) and their efficiency is as measured in the text.

TABLE 1

Sequence of morpholino oligonucleotides and synthetic peptides

| Morpholino oligonucleotides: | |
|---|---|
| CAT: | CTGACTGAAATGCCTCACCA (SEQ ID NO: 26) |
| Gyr241: | GACCGCCGAGTCACCACCA (SEQ ID NO: 27) |

TABLE 1-continued

Sequence of morpholino oligonucleotides and synthetic peptides

| | |
|---|---|
| Gyr 313: | GTTACCCTGACCGACCA (SEQ ID NO: 14) |
| MMb1a: | GGTTTGAGGGACACCA (SEQ ID NO: 30) |
| ECb1a: | TAAGGGCGACACACCA (SEQ ID NO: 31) |
| SCR07 (full length) | CTGTTCACTAGCTTGCAA (SEQ ID NO: 32) |
| lac: | CGGTGCGGGCCTCACCA (SEQ ID NO: 37) |
| SCR5: | CTAGC (SEQ ID NO: 33) |
| SCR9; | CACTAGCTT (SEQ ID NO: 34) |
| SCR13: | TTCACTAGCTTGC (SEQ ID NO: 35) |
| Gyr313-14: | ACCCTGACCGACCA (SEQ ID NO: 28) |
| Gyr313-11: | CTGACCGACCA (SEQ ID NO: 29) |
| T11: | TTTTTTTTTTT (SEQ ID NO: 36) |

Peptides:

| | |
|---|---|
| AB1: | YARVRRRGPRGYARVRRRGPRRC (SEQ ID NO: 2) |
| ALT14264: | YARVRRRGPRR (SEQ ID NO: 38) |
| ALT14740: | GPRGYARVRRRGPRR (SEQ ID NO: 39) |
| ALT14741: | VRRRGPRGYARVRRRGPRR (SEQ ID NO: 40) |
| ALT14751: | YARVRRRGPRGYAR (SEQ ID NO: 41) |
| AB2: | YARVRRRGPRGYARVRRRGPRR (SEQ ID NO: 1) |
| AB2Fluor: | Fluorescein-YARVRRRGPRGYARVRRRGPRR (SEQ ID NO: 42) |

Location of Conjugates Inside Bacterial Cells

Fluorescein labeled conjugate (FC) at a concentration of 1 µM was mixed with growing bacteria, incubated for a further 3 h and then samples were taken and examined in a fluorescent microscope (Llopis et al., Nature. 466: 77-81 (2010)). These experiments were repeated with several bacteria including Staphylococcus aureus, Salmonella, and E. coli SM105 using conjugate AB2-FLgyr241. Since the cells were washed extensively after the fluorescent conjugate was added, any fluorescence in the cells likely indicates that the conjugate was internal and not located on the surface of the cells. The number of cells with fluorescein-conjugate in vivo was about 90% of total E. coli cells, as it was with B. subtilis. For Klebsiella the value of cell integrated fluorescence was about 17% and for Enterococcus and Staphylococcus aureus it was close to zero with respect to the average background in the control cells (Sliusarenko et al., Molecular Microbiology 80: 612-627 (2011)). The viability assays shown below reflect these numbers. However, with S. aureus at 5 µM, the conjugate did inactivate the bacteria (Table 5, below).

General Method for Testing Efficiency of Different Conjugates

Various base sequences were found to be effective as EGSs (Shen et al., Proc Natl Acad Sci USA 106:8163-8168 (2009), Lundblad et al., Proc Natl Acad Sci USA. 105:2354-2357 (2008)) in part by assaying them in vitro as guides of RNase P to the target RNA. After conjugation of the PMO with the relevant base sequence to the peptide to make the compound, the resultant conjugate was added to bacteria growing in liquid culture to test whether the gyrase A target RNA conjugate was effective in killing bacteria and whether drug resistance (chloramphenicol (cat) or penicillin (bla)) cells had also been killed by targeting those genes (see Materials and Methods) as described below.

The Effect of Conjugates are Governed by the Action of RNase P

To ascertain that the results were mediated by the RNase P cleavage mechanism of target RNAs, a typical reaction was analyzed in a RNase P mutant strains of E. coli BW (Wegscheid et al., RNA 12:2135-2148 (2006)). In 10 mM arabinose, the strain made RNase P and it functioned normally. If arabinose was washed out of the growth medium and 0.5% glucose was added, no RNase P was made. Thus, cells were grown overnight in arabinose and were then diluted into fresh medium in two aliquots. One contained glucose and the other arabinose. After 6 h, the cells in glucose showed no effect on viability of two conjugates (500 nM) that contained either gyr313 or a scrambled sequence (Table 2; the characteristics of scrambled sequences are discussed below). However, the strain grown in arabinose showed a viability of approximately $10^{-2}$ after 6 h and a lower viability at 7 h. The data indicate clearly that RNase P functions to cleave whatever sequences are complexed with the specific and partially specific sequences of target RNA.

TABLE 2

RNase P controls the change of phenotypic response

| 6 hr | 10 mM arabinose | 0.5% (w/v) glucose |
|---|---|---|
| gyr 313 | $1.7 \times 10^{-2}$ | 0.5 |
| SCR | $1.3 \times 10^{-2}$ | 0.27 |
| 7 hr | 10 mM arabinose | 0.5% (w/v) glucose |
| gyr313 | $1.8 \times 10^{-3}$ | 2.2 |
| SCR07 | $2.6 \times 10^{-4}$ | 0.68 |

Table 2 shows RNase P controls the change of phenotypic response. E. coli BW was assayed under different conditions as indicated in the text. The assay was done twice at 6 h and once at 7 h. The conjugates used were AB1gyr313 and AB1SCR, both at 500 nM, and viability, measured as colony forming units on agar plates, is indicated in the Table 2.

Example 2

Basic Peptide-Morpholino Oligonucleotide Conjugates Target the Gyrase A Gene

Materials and Methods
See Example 1, above.
Results
The Gyrase A Target Gene
The gyrase A target sequence was examined extensively by database analysis. A conserved region of the gyrase A gene was identified in bacteria and this sequence formed the basis for the EGS in *E. coli* and was useful in testing other bacteria (Shen, et al., *Proc Natl Acad Sci* 106:8163-8168 (2009)). Data on the effectiveness of the low concentration of the conjugate that targeted the gyrase A gene are shown in Table 3A. The viability of bacteria after 6 h of mixing was 7.7×10$^{-5}$ for two separate conjugates tested at 5 µM (only one is reported in the Table 3B, gyr 313).

TABLE 3A

Assays for killing of bacteria that contained genes targeted to chloramphenicol (Cm) and ampicillin (bla) resistance

| Conjugate | Concentration (mM) | Viability |
|---|---|---|
| AB1 CAT | 9 | 4.4 × 10$^{-4}$ |
| " | 5 | 3.4 × 10$^{-4}$ |
| " | 0.5 | 9.7 × 10$^{-3}$ |
| AB1 bla | 5 | 4.3 × 10$^{-4}$ |
| " | 1 | 5 × 10$^{-4}$ |

TABLE 3B

Assays for killing of bacteria by the gyrase A conjugate

| AB1 gyr313 | 5 | 7.7 × 10$^{-5}$ |
|---|---|---|
| " | 0.5 | 1.4 × 10$^{-2}$ |

Tables 3A and 3B show loss of viability of bacterial phenotype after mixing with the CPP-PMO conjugate. Cells were grown in LB broth as described in Materials and Methods and mixed with a conjugate with the relevant base sequence after dilution from an overnight culture. Viability was assayed after 6 h for the AB1 gyr assay. The host cells were *E. coli* BL21/pACYC and SM105 for Cm at 0.5 µM at 4 h. *E. coli* BL21/pUC19 was used for the bla experiment and was assayed at 6 h after conjugate addition. At least two experiments were done in each case. The peptide used was abbreviated as AB1

The phenotypic change was from live to dead bacteria. Bacteria that differed from the *E. coli* gyrase A sequence by only a few nts (Table 4) could be tested with the same conjugate since a mismatch of 3 nt out of 12 had little effect on the success of the EGS sequence (McKinney et al., *Proc Natl Acad Sci USA* 98:6605-6610 (2001) if the 3 nt are not contiguous or are not located close to each other. Table 5, described below, illustrates the results of a screen of different bacteria with even lower concentrations of the conjugate.

TABLE 4

Alignment of gyrA-313 sequences

| gyr-313 | GTTACCCTGACCGACCA (SEQ ID NO: 14) |
|---|---|
| Escherichia coli | CGGTCAGGGTAAC (SEQ ID NO: 4) |
| Acinetobacte | CGGTCAGGGCAAC (SEQ ID NO: 5) |
| Bacillus subtilis | CGGTCACGGAAAC (SEQ ID NO: 6) |
| Enterobacter cloacae | TGGCCAGGGTAAC (SEQ ID NO: 7) |
| Enterococcus faecalis | CGGCCACGGAAAC (SEQ ID NO: 8) |

TABLE 4-continued

Alignment of gyrA-313 sequences

| Klebsiella pneumonia | CGGCAGGGTAAC (SEQ ID NO: 9) |
|---|---|
| Mycobacterium marinarum | CGGTCAGGGCAAC (SEQ ID NO: 5) |
| Pseudomonas syringae | CGGTCAGGGCAAC (SEQ ID NO: 5) |
| Salmonella enterica ssp. typhimurium | TGGTCAGGGTAAC (SEQ ID NO: 12) |
| Staphylococcus aureus | TGGCCAAGGTAAC (SEQ ID NO: 13) |

The nature of the gyrase A gene as a pivotal target in the viability of bacteria (Wang, *Nat Rev Mol Cell Biol* 3:430-40 (2002)) was shown in the experiments. This gene, in which a segment of its sequence is well conserved throughout bacteria, proved a valuable target for EGSs technology even though for some bacteria there were changes of a few nucleotides in comparison with the standard, *E. coli*. Although it is a simple matter to change the sequence of an EGS for *E. coli* to one appropriate for other bacteria, in fact, the same EGS works against a number of bacteria if only a few nucleotides differ in the sequence of the conserved gyrase A region (McKinney et al., *Proc Natl Acad Sci USA* 98:6605-6610 (2001)). Some discussion of the bacterial specificity is given below although it is appropriate to indicate that some of the bacteria, even if they only differ by three nucleotides compared to the *E. coli* sequence, may affect viability considerably (e.g. *E. faecalis, M. marinum* and *E. cloacae*). It is necessary to make conjugates in which the PMO has the identical sequence to the genome being targeted, as has been done for *S. aureus* (Table 5).

TABLE 5

Summary of different bacteria tested for sensitivity to different conjugates

| Bacterium | Conjugate | Conc. (mM) | Viability |
|---|---|---|---|
| E. coli | AB2-gyr313-14 | 0.5 | 10$^{-6}$ |
| S. typhimurium | gyr313-14 | 0.5 | 10$^{-3}$ |
| B. subtilis | gyr313-14 | 0.5 | 6 × 10$^{-6}$ |
| P. syringae | gyr313-14 | 2 | 6 × 10$^{-2}$ |
| Acinetobacter | gyr313-11 | 0.5 | 3 × 10$^{-3}$ |
| K. pneumoniae | gyr313-14 | 0.5 | 4 × 10$^{-5}$ |
| S. aureus | Sagyr313-14 | 5 | 7.5 × 10$^{-4}$ |
| Enterobacter | AB1-CAT | 5 | 0.02 |
| Enterobacter | AB2-gyr313-11 | 5 | 0.08 |
| S. aureus | AB2-gyr313-14 | 1 | 0.30 |
| E. faecalis | AB2-gyr313-11 | 2 | 0.03 |
| M. marinum | AB1-mmbla | 1 | 0.27 |
| M. marinum | AB1-gyr313 | 1 | 0.12 |

Table 5 shows a summary of different bacteria tested for sensitivity to different conjugates. *M. marinum* was assayed after two days of inclusion of the conjugates at 30° C. and was also incubated for one day from an overnight culture. The full length conjugates had a morpholino oligonucleotide of 17 nt plus ACCA at their 3' termini. All assays in the top part of the table were at 6 h after administration of the conjugate. Assays in the bottom of the table for AB1 conjugates were assayed after 4 h. The last two digits at the end of the AB2 designation indicate the number of nts in the PMO. The one conjugate preceded by Sa was designed with specific complementarity to S. auerus gyrase gene. Tests were done as described in the legend to Table 2. Viability of CPP alone in the top part of the table are greater than 0.5 at 1 µM or higher. All the conjugates in the top part of the table are AB2.

Scrambled Sequences

Conjugates with scrambled sequences were effective as controls with the original PPMOs used (Shen et al., *Proc Natl Acad Sci USA* 106:8163-8168 (2009)) in that they showed no decrease in viability of test strains under the conditions where gene-targeted PPMOs did. However, with the new CPP in the conjugates used here, scrambled sequences in the morpholino oligonucleotides had a significant effect on viability (Table 6).

TABLE 6

Killing kinetics with scrambled sequence conjugates

| Conjugate | | Viability |
|---|---|---|
| AB1 SCR 18 (CTGTTCACTAGCTTGCAA) | (SEQ ID NO: 32) | $2.3 \times 10^{-4}$ |
| AB1 SCR 13 (TTCACTAGCTTGC) | (SEQ ID NO: 35) | $2.7 \times 10^{-4}$ |
| AB1 SCR 9 (CACTAGCTT) | (SEQ ID NO: 34) | $5.6 \times 10^{-3}$ |
| AB1 SCR 5 (CTAGC) | (SEQ ID NO: 33) | $1.2 \times 10^{-3}$ |
| AB1 gyr313 | | $1.0 \times 10^{-3}$ |
| AB2 SCR 18 | | $6.9 \times 10^{-4}$ |
| AB2 SCR 9 | | $2.9 \times 10^{-4}$ |
| AB2 gyr313-14 | | $2.9 \times 10^{-4}$ |

Table 6 shows killing kinetics with scrambled sequence conjugates. *E. coli* SM105 was the host bacterium and the assay was done after 6 hr incubation with the conjugate at 500 nM. The number following SCR is the number of nucleotides in the conjugate. The results shown are the average of two experiments.

In fact, the scrambled sequences had partial complementarity to various RNAs as judged by genomic searches in *E. coli*. The new CPP-PMO conjugates reported here, which have more favorable binding to target RNAs and stabilized the complexes made with conjugates (see below), yielded the result in the table. These data indicate that the power of the technique reported here to decrease cell viability extends well beyond the extended matches made to specific gene sequences. Sequences with only 5 or 9 nt of complementarity also decrease cell viability. This would only be expected if the CPP in the conjugates had extremely strong binding to a region of target RNA (or DNA) in vivo to which a small sequence, of e.g. five nts, has complementarity. In fact, SCR-9 was less effective compared to the other scrambled sequences in the table in decreasing cell viability at lower conjugate concentrations (data not shown). The effectiveness of SCR 9 was also about 70-fold less than AB2-gyr313-14 as a function of concentration from 50 nM to 1 µM (data not shown). AB2-T11, which has a sequence of 11 consecutive T's, had no effect at concentrations up to 500 nM but did have a 20% decrease in viability at 1 µM (data not shown). This sequence would be a suitable control for most reactions reported here.

When AB2 synthesized by Biopeptides was used as the CPP (Table 5), the effective concentration of the resulting conjugate was several-fold lower than that of AB1.

Summary

Control experiments with "scrambled" base sequences in the morpholino oligonucleotide yielded surprising results in that these conjugates also killed bacteria in a manner that did not target specific gene sequences. That is, in attempts to alter drug resistance of bacterial strains or to alter the expression of nonessential enzymes, strains were killed by scrambled sequences. In fact, scrambled sequences have considerable homology to many sequences in a bacterial genome at levels that do not necessarily include the full length sequence that, for example, altering drug resistance requires. This conclusion concerning loss of viability is not true of conjugates that have a much shorter peptide sequence (Shen et al., *Proc Natl Acad Sci USA* 106:8163-8168 (2009)). This supposedly non-specific effect of killing by scrambled sequences might require the action of RNase P. The strong binding of the novel basic peptide in the conjugates described here to any piece of nucleic acid leads to a very tightly bound complex of the conjugate with an RNA that might only have five complementary nts. In this sense, the mode of killing has little to nothing to do with targeting a specific gene, although the latter must be part of the inactivation of the expression of genes. It is possible that tightly bound complexes described here may alter normal processes of translation, transcription or replication inside cells, certainly in the latter case if the complexes also form with single stranded DNA as a prelude to transcription or replication.

Example 3

Basic Peptide-Morpholino Oligonucleotide Conjugates Induce Drug Susceptibility in Drug Resistant Bacteria Materials and Methods
See Example 1, above.
Results
Drug Resistance Conjugates were added to growing bacteria to test whether cells harboring drug resistance (chloramphenicol (cat) or penicillin (bla)) had resulted in the cells killed by inactivation of expression of the cat and bla genes.

An examination of data bases showed that a sequence in the gene for Cm resistance that was used successfully for an EGS (Guerrier-Takada et al., *Proc Natl Acad Sci* 94: 8468-8472 (1997)) was in fact completely homologous (100% sequence identity) to a 12 nt sequence of several different genes in *E. coli* and several other bacteria. As the stringency was lowered in this test, many more sequences in different genes showed homology to partial sequences of the cat gene. In fact, a test of this sequence in the conjugate, showed a loss of viability on several bacteria in the presence or absence of Cm in LB broth used for assays (data not shown). In fact, the gene for Cm resistance did function well for assays in the system as shown in Table 3A. The viability of *E. coli* after administration of the conjugate dropped to about $5 \times 10^{-4}$ when the assay was done at 4 h after administration but this compound was still effective at lower concentrations, e.g., 500 nM, rather than the 5 µM used in most other experiments. While the results with more than one concentration of CPP-PMO are given here, it is useful to note that using a lower concentration (500 nM), which may not be as effective as an agent at higher concentration (5 µM), might still be practical in experiments with animals. It should also be noted that when the conjugate targeted to Cm resistance is added in conjunction with a conjugate targeted to the gyrA mRNA, each at 100 nM, the viability of cells decreased to about $10^{-2}$ from about 0.5 (data not shown) when the conjugates were added separately as has been noted before with a different experimental system (16).

As a quick assay to determine if cells were susceptible to the peptide, either the peptide alone was added to a growing culture or the peptide was added simultaneously with the chloramphenicol (CAT) PMO alone; viability was examined at 4 h of culture growth. The results of such assays (9 samples) showed the viability with CPP drops in *E. coli* to about 0.7, or 0.63 for cells with plasmids, compared to control cells when nothing is added for concentrations of the peptide of 5 µM. Viability goes up as the peptide concentration is lowered. However, when the PMO is added non-covalently with the CPP, viability decreases about 30% compared to when CPP was present alone, an indication that the bacteria tested are susceptible to the CPP-PMO treatment (data not shown). No decrease in viability was seen when PMO was added by itself.

There is more than one mode of resistance to penicillin in many bacteria as judged by database searches. An EGS was used with success against the penicillin resistance gene in *E. coli* (Guerrier-Takada et al., *Proc Natl Acad Sci USA* 94: 8468-8472 (1997)). When possible, the same conjugate was used for other bacteria. In other cases, new conjugates will have to be made. For the conjugate with the previously successful EGS sequence (Wegscheid et al., *RNA* 12:2135-2148 (2006)), the viability of bacteria in which the bla gene was located on a multi-copy plasmid was $4.3 \times 10^{-4}$ at 5 µM, somewhat higher at 1 µM (Table 3A).

The effective concentration of the conjugate in the experiments in Tables 3 and 5 was between 500 nM and 5 µM. This is at least 10- to a 100-fold more effective than previous measurements with CPPs in conjugates made by AVI Biopharma (Shen et al., *Proc Natl Acad Sci USA* 106:8163-8168 (2009)). In particular, the lowest values achieved were for *B. subtilis*, discussed below, as determined earlier with an AVI Biopharma CPP.

Various *E. coli* strains grown with a conjugate that targeted the bla gene in the absence of ampicillin were also depleted in viability. These data, as was the case for the Cm gene noted above, indicated that partial homologies with non-targeted sequences is an important fact with conjugate that have the 23 amino acid residue sequence. The conjugate must bind more tightly to segments of the partly homologous nucleic acid than had been indicated by binding of nucleic acid sequences directly. There are two exceptions: one was the strain BL21/pUC19 that contains a plasmid coding for bla resistance and the other was strain BL21/pACYC that contains a plasmid coding for the Cm resistance gene. In the presence of ampicillin, BL21/pUC19 decreased in viability compared to strains with the bla gene on the chromosome by a factor of about 10. BL21/pACYC was decreased in viability about 100 fold more than strains that were either Cm resistant or non-resistant in the presence of chloramphenicol. it was also noted that the mmbla conjugate had an effect on the viability of *E. coli* but virtually none (10-fold lower on *E. coli*) on *M. marinarum*. These data indicate that the primary, but certainly not complete, cause of loss of viability results from the toxic effects of the conjugate on the bacteria used and is discussed below.

The utility of drug resistance genes is not quite as universally useful as that of the gyrase A gene. Here, for chloramphenicol and ampicillin, there is a much greater variability in base sequence and, in fact, in the gene or genes that affect drug resistance of penicillin or ampicillin. In these cases, the ability of the particular conjugate to kill these cells was effective, although not quite as generally remedial as conjugates on the gyrase A gene (Table 3).

Another control that is relevant includes assays with a conjugate targeted to the lac gene in *E. coli*. While attacking the lac mRNA alone should have no effect on cell viability, both a wild type *E. coli* and a strain with a deletion in the lac gene were reduced in viability to about $10^{-4}$ at 500 nM concentration of the conjugate. This is the clearest indication that gene specific targeting, itself, is not responsible for the total effect of the conjugates used. However, in a comparison of gyr conjugates with the intact PMO sequence and a partial gyr sequence, it is apparent that targeting a particular gene does have an effect on viability (Table 5) as was also pointed out with respect to the bla and cm genes in the absence and presence of the appropriate drugs. A full length PMO has a greater effect on viability than does a shorter PMO that also attacks, e.g. the gyrase gene. The small difference in length of the PMO should not make a significant difference in reducing viability though a bacteriocidal action. The proportion of loss of viability due to bacteriocidal action and gene-specific targeting is difficult to judge but the bacteriocidal action seems to have a greater effect. It is also clear that a contaminant in the conjugate preparations is not responsible for the bacteriocidal action since some conjugates, e.g. AB20 T11, have a much lower effect on viability than other conjugates.

Time of Administration of Conjugate

To explore the possibility that an additional mixture of the conjugate would decrease the viability of cells in the experiments, a second administration of conjugate was added 4 h after the first dose. In these experiments, cells were assayed at 6, 8, and 10 h after the first conjugate administration. The results are shown in Table 7 and indicate that the second administration of gyrase A CPP-PMO apparently killed more than 99% of bacteria in cultures of *E. coli* or *B. subtilis*, i.e., about $10^{-6}$ or a lower fraction of cells survived. Furthermore, the results showed that the time from the first administration of conjugate was optimal at 6 h.

Effect on Other Pathogenic Bacteria

A survey of the effects of different conjugates on other bacteria is presented in Table 5. The table shows viability results with particular conjugates used that are perfectly matched in base sequence complementarity with *E. coli* genes. However, a new conjugate was also made that was perfectly matched in base sequence complementarity to the *S. aureus* gyrase gene. This conjugate was successful in reducing the viability of *S. aureus* to $7 \times 10^{-3}$ at 5 µM and lower by a factor of roughly two at 10 µM. The addition of the conjugates was bacteriocidal and obviously reduced viability, e.g., for *Acinetobacter* and *Klebsiella*. Results of assays of other bacteria are shown in Table 5.

TABLE 7

Time course of mixture with conjugates

| | | Assay (hr): | | | |
|---|---|---|---|---|---|
| Bacterium | Conc. | 4 | 6 | 8 | 10 |
| *E. coli* | 5 µM | $3 \times 10^{-4}$ | $1.2 \times 10^{-6}$ | $<10^{-6}$ | $6 \times 10^{-6}$ |
| No added mix | " | $3 \times 10^{-4}$ | $<10^{-5}$ | $9 \times 10^{-6}$ | $6 \times 10^{-6}$ |
| *B. subtilis* | 0.5 µM | $7.3 \times 10^{-4}$ | $2.5 \times 10^{-5}$ | | |
| No added mix | " | $7.3 \times 10^{-4}$ | $1.6 \times 10^{-3}$ | | |

Table 7 shows a time course of mixture conjugates. Assays were carried out as described in Table 2. Controls are cells with no additional conjugate at 4 hr. Otherwise there was an additional conjugate at 4 hr. The conjugate used was AB1gyr313. Viability of CPP alone varied between 0.5 and 0.7.

In this case, the effects on *E. coli* and *Bacillus subtilis* W168 are remarkable, as observed previously (13), for their effectiveness at low concentrations of the conjugate. *P. syringae* and *Acinetobacter* were also severely affected by the gyrase CPP-PMO. Apparently an *Enterococcus* strain that is not identical to its most pathogenic relatives is decreased somewhat in viability at 5 µM, but not enough to justify its use as a therapeutic agent with the *E. coli*-specific gyrase A conjugate. *Mycobacterium marinum* did show a slight decrease in viability in the presence of a conjugate for penicillin resistance. The other bacteria listed had to be investigated further for their potency as a function of concentration. Note that the CPP-PMO used was specific for the *E. coli* gyrase A sequence. A difference of more than 3 nt from the *E. coli* sequence implies negative results. It was previously determined that various naked RNA EGSs, administered by a biological process in which synthetic genes coding for certain functions were transcribed, were also effective in decreasing the expression of the genes that controlled virulent functions in dangerous, pathogenic bacteria (Lundblad et al., *Proc Natl Acad Sci USA*. 105:2354-2357 (2008)).

The minimum inhibitory concentration ($MIC_{50}$) for *E. coli* is 0.4 µM with AB2gyr313 as determined by standard procedures. The $MIC_{50}$ for *S. aureus*, with a conjugate made specifically for that bacterium against gyr313, is 8 µM. No $MIC_{50}$ was measured with the other bacteria that lack perfect homologies in sequence between the PMOs designed against *E. coli* genes and the corresponding genes for the other bacteria except for mmbla for *M. marinarum*, which was not inhibitory.

Many of the tests listed in Table 5 were performed with AB2-T11 (1 µM) as a control, which had a viability of 0.5 on average.

Example 4

Basic Peptide-Morpholino Oligonucleotide Conjugates Bind More Tightly to RNA than does the Naked RNA EGS Materials and Methods
See Example 1, above.
Approximate Determination of Melting Temperatures of Different Complexes
Conjugates
Complexes with conjugate (0.5 pmol) and target RNA (0.1 pmol) were run in 1.5% agarose gels with buffers as described in Talbot and Altman (Talbot et al., *Biochemistry* 33: 1399-1405.). mRNA alone was incubated for 5 min at room temperature. Samples (10 µL) in binding buffer (Talbot et al., *Escherichia coli. Biochemistry* 33: 1399-1405 (1994)) were incubated at 37° C. for 15 min and then 10 min for the designated temperatures, placed on ice for 5 min and were loaded on a 1.5% agarose gel and run for about 1.5 h at 110-130 mAmp and 100 V. RNA: gyrA mRNA from *E. coli* (206 nt); conjugate: AB1gyr313; PPMO gyr313. Controls of each sample prepared on ice were also run and did not differ in migration from RNA alone at each temperature. Each temperature set contained the RNA alone, incubated for 5 min at 37° C. prior to addition of the rest of the sample in each case, and the conjugates AB1gyr313 and then PPMO gyr313 are in each set. Incubation at 30° C.; 37° C.; 45° C.; 55° C.; or 90° C.

Complexes with Naked RNA EGS
Complexes with naked RNA EGS (5 pmol per reaction) and target RNA (0.1 pmol per reaction). The samples were treated as described above except that incubation of the total mixture was for 20 min at room temperature and then 20 min at the designated temperature below and the samples were put on ice before loading on gels. Electrophoresis was in a 12% polyacrylamide gel with the following freshly made buffer for 6 h and 50-60 mAmp at 200V: 50 mM Hepes, pH 8, 50 mM KCl, 1 mM Mg acetate. Incubation at 30° C.; 37° C.; 45° C.; 55° C.; or 90° C. Experiment was repeated with the CAT conjugate AB1 CAT and the gyr313 RNA; and AB1gyr313 conjugate and CATmRNA.

Results
Complexes of Conjugates with Target RNA Analyzed by Electrophoresis in Gels
Intact, double stranded RNA complexes can be distinguished from complexes made with the conjugates described here by a gel retardation assay (Talbot et al., *Escherichia coli. Biochemistry* 33: 1399-1405 (1994)). Two conjugates, AB1gyr313 and PPMO gyr313 (Shen et al., *Proc Natl Acad Sci USA* 106:8163-8168 (2009)) were tested in these reaction with a $^{32}$P-labeled mRNA that contained the gyr313 sequence. If the complexes were heated to 90° C. and rapidly cooled, the target RNA now migrated with the control band if the complex had been denatured. If this experiment is repeated at different temperatures, the melting temperature of the conjugate should be measured accurately. The naked RNA EGS:mRNA complex showed this behavior when added at a high concentration. About 10% of the mRNA was complexed with the EGS as detected quantitatively by this method and at temperatures at 65° C. or higher, the amount of complex is decreased. The RNA degraded into oligo- and mononucleotides at the high temperature for longer periods of time at 90° C. More important are the negative controls in which the CAT conjugate AB1CAT did not show any binding to the gyr313 RNA and AB1gyr313 does not show any binding to the CATmRNA. This approximate method of measuring melting energy of the complex indicated that the complex with the conjugate had a higher binding energy than one with naked RNA in the complex although their base sequences are identical. These experiments give credence to the notion that the conjugate binds more tightly to RNA than does the naked RNA EGS, and supports the binding of the conjugates to partial homologous sequences in bacteriocidal action.

Example 5

The EGS Oligonucleotide Directs Cleavage of the *P. Falciparum* Gyra mRNA in Vitro by Human Rnase P Materials and Methods
Strains and Culture Conditions
*P. falciparum* strains 3D7, Hb3, W2 and Dd2 were used and cultured using standard growth condition (Trager, et al., *Science* 193(4254):673-675 (1976)) modified by replacing human serum with 0.5% Albumax I (Invitrogen).
Synthesis of the Conjugates
The method used was similar to that described in Example 1 above.

Preparation of RNase P and Substrates

The preparation of human RNase P is described in (Guerrier-Takada, et al., *Methods Enzymol* 313:442-456 (2000)).

Substrates were prepared as described in (Guerrier-Takada, et al., *Methods Enzymol* 313:442-456 (2000)) (Guerrier-Takada, et al., *Proc Natl Acad Sci USA* 94(16):8468-8472 (1997)).

Results

The gyrase A gene from *E. coli* harbors a short sequence, which is highly conserved across many bacteria, and has successfully been targeted for RNase P-mediated degradation (Wesolowski, et al., *Proc Natl Acad Sci USA* 108(40): 16582-16587 (2011)). This sequence is also partially conserved in the gyrA gene of *P. falciparum*, which should play an essential function in parasite replication (FIG. 2).

The sequence utilized in the experiments is a target for the complementary EGS and as part of a chemically derived morpholino oligonucleotide (MO). Interestingly, this sequence is different from that in the human topoisomerase II TopoII gene by three nucleotides and two of them are contiguous in the region important for the action of the EGS (Table 8).

TABLE 8

Sequence alignment of the EGS-targeted regions

| Organism | Target DNA sequence |
|---|---|
| E. coli | CGGTCAGGGTAACTTCGGT$^{330}$ (SEQ ID NO: 15) |
| P. falciparum | AGGTTATGGTAATTTTGGT$^{825}$ (SEQ ID NO: 16) |
| P. yoelli | TGGATATGGTAATTTTGGG$^{870}$ (SEQ ID NO: 17) |
| P. berghei | CGGATATGGTAATTTTGGA$^{786}$ (SEQ ID NO: 18) |
| H. sapiens | TGATTATTATAATTTTGAG$^{6457}$ (SEQ ID NO: 19) |

Sequence alignment of the EGS-targeted regions in the *E. coli*, *P. falciparum*, *P. yoelli* and *P. berghei* gyrase A genes and the *H. sapiens* TOP2A (topo II) gene. Numbers at right are the positions in the sequence alignment of the gene of the last 3' nucleotide in this particular segment. Bold fonts are the complements of the nucleotides in the EGSs that were made in this study.

TABLE 9

Sequences of EGS

| CPP-MO | Sequences 5' to 3' |
|---|---|
| Ecgyr f.1.EGS | 5'-GAA*G*UACGAAGGUUCGAAUCCUUCCC*CUG*ACUGGU-3' (SEQ ID NO: 20) |
| Ecgyr EGS | 5'-GAA*G*UACGAGGUUCGAAUCCUCCC*CUG*ACUGGU-3' (SEQ ID NO: 21) |
| Plfgyr f.1.EGS | 5'-GAA*A*UACGAAGGUUCGAAUCCUUCCC*CAUAA*CUGGU-3' (SEQ ID NO: 22) |
| Plfgyr EGS | 5'-GAA*A*UACGAGGUUCGAAUCCUCCC*CAUAA*CUGGU-3' (SEQ ID NO: 23) |
| Plfgyr2 EGS | 5'-GAA*A*UACGAGGUUCG<u>UG</u>CCCUCCC*CAUAA*CUGGU-3' (SEQ ID NO: 24) |
| PlfgyrΔ2bp EGS | 5'-GAA*A*UACGAGGUUCGA--CCUCCC*CAUAA*CUGGU-3 (SEQ ID NO: 25) |

Sequences of EGSs used in Example 5. Bold, capital letters are part of the EGS sequence. Italicized letters show differences between *E. coli* and *P. falciparum*.

Underlined are the changes made in a second EGS. Hyphens represent the two nucleotides deleted in the stem-loop structure of the EGS. An EGS RNA (FIG. 2), with a structure required for recognition by an eukaryotic RNase P, was cloned (Meissner, et al., *Proc Natl Acad Sci USA* 102(8):2980-2985 (2005)), and incubated in vitro in the presence of a $^{32}$P labeled mRNA segment of PfGyrA in the absence or presence of RNase P. The reaction products were subsequently separated by electrophoresis on the basis of their molecular size. Like other successful EGS (Guerrier-Takada, et al., *Methods Enzymol* 313:442-456 (2000)), the EGS complementary to PfGyrA produced the anticipated fragments with a relatively crude fraction of RNase P from HeLa cells while an EGS targeting the *E. coli* gyrase mRNA did not cleave this construct. Consequently, conjugates were synthesized with the corresponding MO and tested for their ability to be transported inside the parasite and to inhibit the growth of *P. falciparum* during its intraerythrocytic development.

Example 6

Fluorescent-Labeled Conjugate is Transported into Malaria Parasites

Materials and Methods

Localization of a Fluorescent Conjugate in *P. falciparum*

A highly synchronized late-Ring stage culture was mixed with 3 μM of CPPFL-MO (conjugate covalently bound to fluorescein) or RPMI (negative control). The culture was incubated for 18 h and samples were collected at different time points. Cells were harvested by centrifugation and washed with RPMI. Cells were placed on slides and covered with glass coverslips. Cells were immediately viewed under a Nikon Eclipse TE2000-E microscope equipped with 100× objective and Roper CoolSNAP HQ camera. The images were analyzed using Meta Imaging.

Results

To assess the ability of the conjugates to enter Plasmodium-infected erythrocytes and to examine the effect of D- versus L-amino acid on the delivery of the conjugates, a fluorescein derivative of the cell penetrating peptide-MO (CPP-MO) was employed. Fluorescent conjugates containing either 5 D- or L-arginines (Table 2) and in which the dye is linked to the amino terminus of the conjugates, were added to a culture of ring stage parasites and parasites were examined at different times points during the intraerythrocytic life cycle of the parasite.

TABLE 10

Peptide sequence used in the conjugates (SEQ ID NO: 1)
Tyr Ala Arg Val Arg Arg Arg Gly Pro Arg Gly Tyr Ala
Arg Val Arg Arg Arg Gly Pro Arg Arg

Residues marked in bold were D forms that were used in the fluorescent conjugate mentioned in the text. In all other experiments, all residues were L forms.

A fluorescein labeled CPP-MO was added at 3 µM to a highly synchronized late-ring stage culture and the incorporation into the parasite was followed by fluorescent microscopy. Fluorescence microscopy analysis revealed that within 30 min, the conjugates could be readily detected within infected erythrocytes and inside the parasite. After 90 minutes, most of the fluorescence was detected inside the parasite. Cultures maintained for 18 h, in which parasites evolved to an early-schizont stage also exhibited fluorescence suggesting a high stability of the conjugate. No fluorescence could be detected in uninfected red blood cells.

This result indicates that the trafficking of the conjugates is mediated by permeation pathways or selective transporters on the plasma membrane of the infected erythrocyte and parasite plasma membrane. Interestingly, the fluorescence signal of the conjugate containing five D-arginine residues was at least 1000-fold stronger than that of a similar conjugate with all L-arginine residues. The stability of the fluorescent conjugate is a remarkable indicator of the utility of such compounds as drug candidates.

As with other oligonucleotide-based technologies, the challenge resides in the ability of the construct to be delivered into the infected erythrocyte. The studies using fluorescently labeled conjugates indicate that they rapidly traffic into the infected erythrocyte. No fluorescence was detected in uninfected erythrocytes, indicating that these constructs do not readily enter red blood cells. Infection of erythrocytes by P. falciparum is accompanied by major changes in the erythrocyte membrane, which result in increased permeability to a large number of substrates, many of which are essential nutrients such as sugars, purine nucleosides and nucleobases, vitamins and amino acids (Kirk, et al., Curr Drug Targets 8(1):75-88 (2007)), (Saliba, et al., Int J Parasitol 31(12):1321-1330 (2001)). Once inside the red blood cytoplasm these precursors are transported inside the parasite by specific permeases expressed on the parasite plasma membrane (Kirk, et al., Curr Top Microbiol Immunol 295: 325-356 (2005)), (Martin, et al., Mol Microbiol 74(3):519-528 (2009)), (Martin, et al., Genome Biol 6(3):R26 (2005)). The selective delivery of the conjugates into infected erythrocytes, but not uninfected erythrocytes, indicate that they may likely use the new permeation pathways (Kirk, Physiol Rev 81(2):495-537 (2001)) on the red blood cell membrane and possibly an oligopeptide permease on the parasite plasma membrane.

Example 7

The CPP-MO Conjugate Inhibits P. Falciparum Development and Reduces Pfgyra mRNA Expression Materials and Methods
SYBR Green-Based Parasite Growth Assay This proliferation assay was adapted from the Malaria SYBR Green I-Based Fluorescence Assay (Johnson J D, et al., Antimicrob Agents Chemother 51(6):1926-1933 (2007)). CPP-MO was added to a 96-well plate with final concentrations stated in text. A highly synchronized early ring stage parasite culture was added to the plate containing conjugate. Controls were performed using non-infected erythrocytes, infected erythrocytes without conjugate, and infected erythrocytes treated with 1 µM CQ (3D7 strain) or 2.5 µg/ml of blasticidin (Hb3, W2 and Dd2 strains) as controls. Plates were incubated for 72 hours at 37° C. in a gas chamber. After 72 hours, erythrocytes were lysed with (20 mM Tris (pH 7.5), 5 mM EDTA, 0.008% saponin, 0.08% Triton-X 100, 1×SYBR Green I) and incubated for 1 h in the dark at room temperature. Plates were read at 497/520 nm on a Synergy MX, Biotek fluorescent plate reader.

Analysis of Gene Expression by qPCR

The Plfgyr EGS-based CPP-MO was added at 4 nM to late-ring/early trophozoite synchronized cultures at 10% parasitemia (2% hematocrit) and the cultures were incubated for 4 hours at 37° C. Total RNA extraction from untreated and treated parasite cultures was performed as previously described (Kyes, et al., Mol Biochem Parasitol 105(2):311-315 (2000)) and the concentration of RNA was determined using a NANODROP®. RNA samples (800 ng of total RNA) were treated with 1 U of RQ1 DNase (Promega) and the absence of DNA contamination was checked by Real-Time PCR. cDNA were then synthesized from total RNA (250 ng) using iScript™ cDNA Synthesis kit (Bio-Rad). Real-Time PCR was carried out using Quantitect SYBR Green PCR kit (Qiagen) using the Applied Biosystems 7500 real-time PCR system. The data were analyzed using the comparative critical threshold (ΔΔCt) method in which the amount of target RNA (gyrA) was compared to Pf-β-actin1 which served as an internal control as previously described (Ferreira, et al., Malar J 5:1 (2006)). Primers used for qPCR are listed in Table 11.

TABLE 11

Primer sequences

| Target | Forward primer (5' → 3') | Reverse primer (5' → 3') |
|---|---|---|
| Pf-β-actin1 | AAAGAAGCAAGCAGGAATCCA (SEQ ID NO: 43) | TGATGGTGCAAGGGTTGTAA (SEQ ID NO: 44) |
| PfgyrA | TCATCCACACGGTGATAAGAG (SEQ ID NO: 45) | GCTGCAGCGTTATATTCAACA (SEQ ID NO: 46) |

Results

Figure 3A:
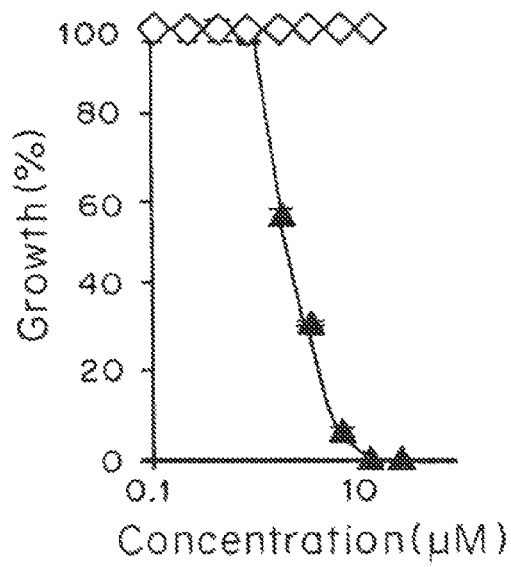
FIG. 3A is a graph showing the effect of treatment with increasing concentrations CPP-MO (μM) targeting either the *P. falciparum* PfGyrA (filled triangles) or the *E. coli* bla mRNAs on the growth of the parasite during its intraerythrocytic life cycle (diamonds) in *P. falciparum*-infected erythrocytes. Growth assays were performed using a SYBR Green I assay (see Materials and Methods) after culturing parasites for 72 h at 37° C. in the presence of the conjugates. Results are a mean of triplicate experiments±SD.
Figure 3B:
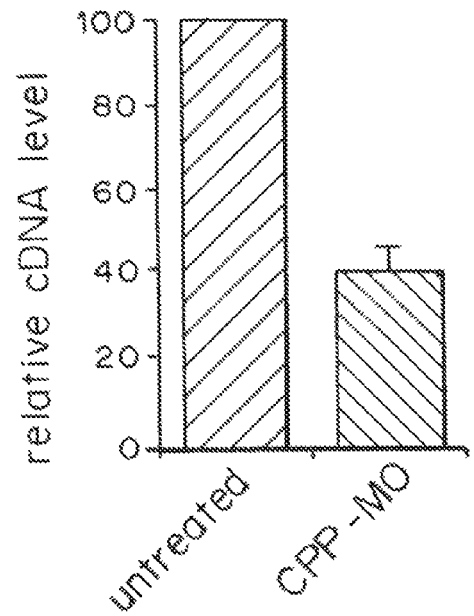
FIG. 3B is a bar graph showing PfGyrA mRNA levels of PfgyrA in the absence (black bar) or presence (gray bar) of EGS-based CPP-MO conjugate measured using qRT-PCR. The Pf-β-actin1 gene was used as an internal control and the relative expression level of PfgyrA in the absence of the conjugate was set to 100. Results are mean of triplicate experiments±SD; $P<0.01$.
Figure 3C:
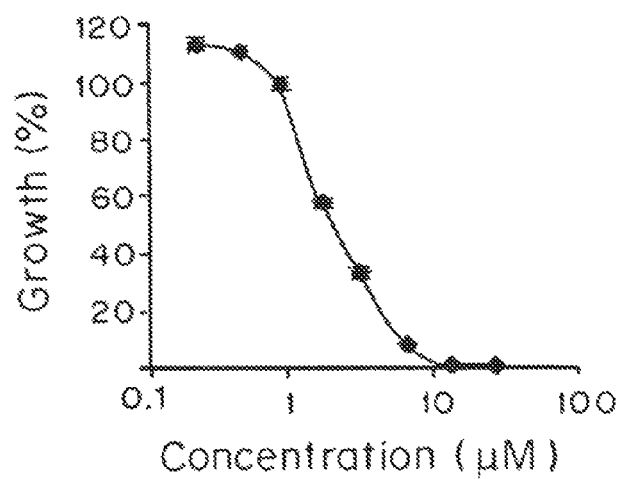
FIG. 3C is a line graph showing growth inhibition of *P. falciparum* 3D7 upon CPP-MO exposure. The graph shows the mean of triplicate experiments plus or minus standard deviation.

To determine the efficacy of the conjugate against the parasite, a synchronized culture of the P. falciparum 3D7 clone at the early ring stage of development was maintained in the absence or presence of increasing concentrations of the conjugate and parasite proliferation was monitored using a SYBR Green I assay. Consistent with results obtained in vitro, the conjugate inhibited the growth of 3D7 parasites with $IC_{50}$ values ranging between 0.8 and 2 µM depending on the batch of the compound (FIG. 3A). The $IC_{90}$ and $IC_{100}$ of the conjugate were reached at ~6.5 µM and ~10 µM, respectively. As a control, a conjugate that targets the *E. coli* ampicillin resistance gene had no effect on parasite proliferation (FIG. 3A). To further demonstrate that the CPP-MO mediates degradation of the PfgyrA mRNA in the parasite, cultures containing primarily late-rings and early trophozoites were maintained in the absence or presence of 4 µM of the Plfgyr EGS-based CPP-MO and total RNA was extracted 4 hours post-treatment and analyzed by qRT-PCR using primers specific to the PfGyrA mRNA. Compared to untreated parasites, conjugate treatment resulted in a 60% decrease in the amount of PfgyrA mRNA (FIG. 3B). As a control, qRT-PCR analysis using primers specific to the *P. falciparum* actin gene showed equal amounts of mRNA in both treated and untreated parasites.

Antimalarial therapy efforts supported by Medicines for Malaria Venture and the World Health Organization have focused on the development of new drugs against validated targets (Anonymous, *PLoS Med* 8(1):e1000402 (2011)). However, because of the limited amenability of *P. falciparum* to genetic manipulation, only a handful of such targets have been validated genetically (El Bissati, et al., *Proc Natl Acad Sci USA* 103(24):9286-9291 (2006)), (Joet, et al., *Proc Natl Acad Sci USA* 100(13):7476-7479 (2003)), (Joet, et al., *Acta Trop* 89(3):371-374 (2004)), (Slavic, et al., *Mol Microbiol* 75(6):1402-1413 (2010)), (Witola, et al., *J Biol Chem* 283(41):27636-27643 (2008)).

For most of the proposed validated targets, the validation is inferred from in silico analyses (Crowther, et al., *PLoS Negl Trop Dis* 4(8):e804 (2010)) or pharmacological studies using inhibitors. However, this latter approach is not reliable because of off-target effects associated with most of those compounds. Large scale efforts to assess the importance of each of the *P. falciparum* 5300 genes is urgently needed and will help not only identify novel drug targets but also better advance the understanding of the biology of this important parasite and its pathogenesis. The success of the CPP-MO approach using the PfGyrA gene indicates that it can be applied to characterize the function of many other *P. falciparum* genes and establish a list of the validated targets, which can be effectively pursued for drug-based therapy.

Example 8

CPP-MO-Mediated Stage Specificity of Inhibition

Materials and Methods

The experiment was initiated using a highly synchronous ring stage culture (8 h following merozoite invasion) at a parasitemia of 3%. Parasites were loaded into a 96-well plate and incubated under standard conditions. At different time intervals, the culture was mixed with 2 µM of the conjugate. Every 8 hours the growth and morphology of the parasite was monitored by light microscopy. Images were collected using a Zeiss microscope equipped with 100× objective and an Infinity Camera.

Results

Figure 4A:
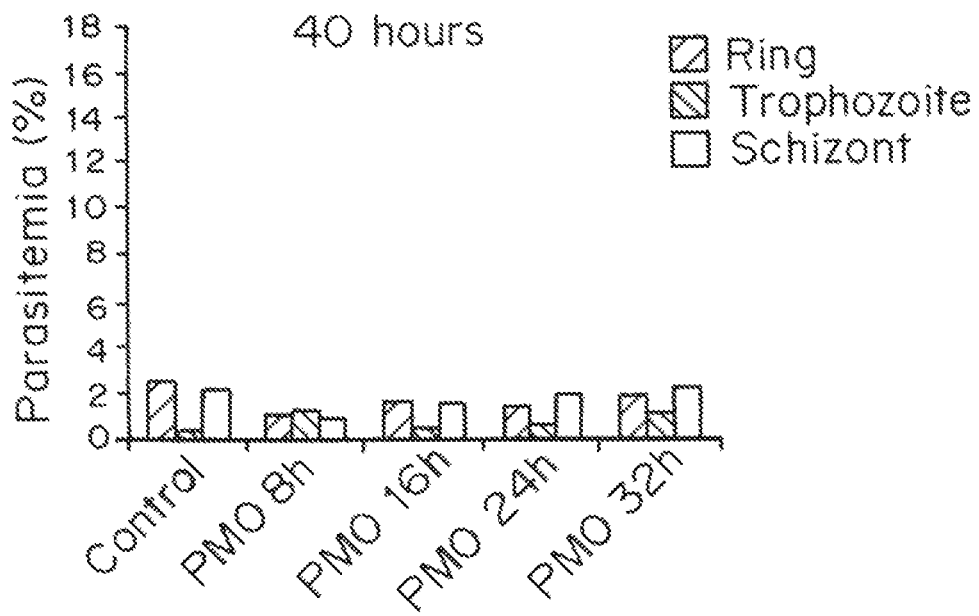
FIG. 4A is a bar graph showing the percentage (parasitemia (%)) of each parasite developmental stage (Ring, Trophozoite, Schizont) 40 hrs after merozoite invasion for control, or PMO treatment for 8 hr, 16 hr, 24 hr, and 32 hr time points.
Figure 4B:
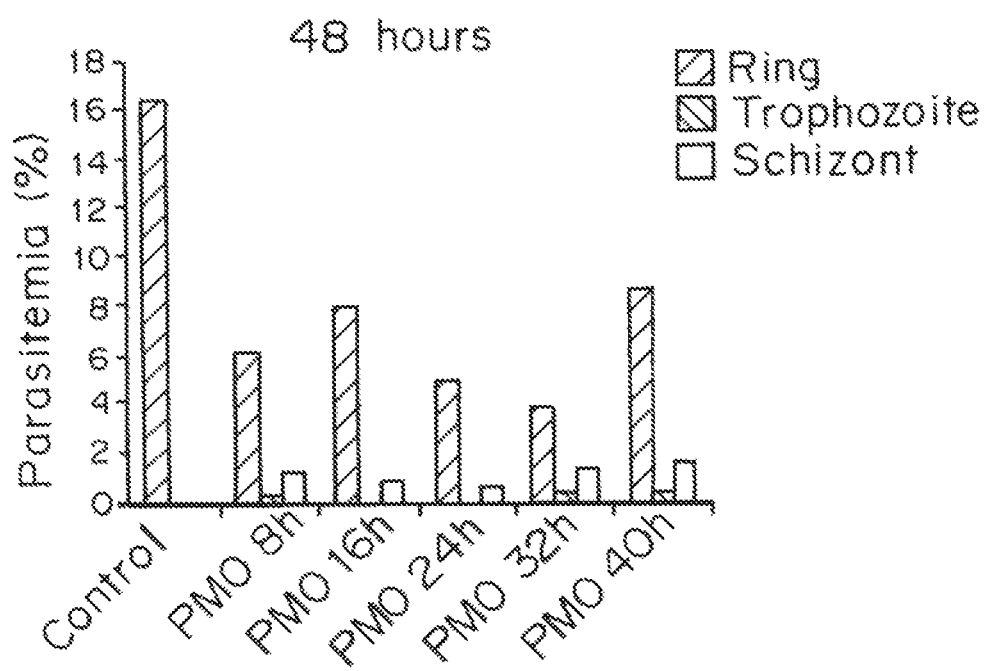
FIG. 4B is a bar graph showing the percentage (parasitemia (%)) of each parasite developmental stage (Ring, Trophozoite, Schizont) 48 hrs after merozoite invasion for control, or PMO treatment for 8 hr, 16 hr, 24 hr, and 32 hr time points.

Previous studies have shown that PfGyrA is expressed throughout the intraerythrocytic life of the parasite (Guerrier-Takada, et al., *Methods Enzymol* 313:442-456 (2000)). Therefore an examination of the addition of the PfGyrA specific CPP-MO at different stages of parasite development was carried out to see if parasite progression from one stage to the next could be altered. The conjugate was added to a highly synchronized ring stage culture of the parasite at its $IC_{50}$ value at different time intervals and the growth and morphology of the parasites were monitored every 8 hours (FIG. 4). Microscopy analyses revealed that addition of the conjugate at the ring stage resulted in both a delay in parasite progression from one stage to another as well as alteration in the morphology of the parasites. By 40 h, whereas untreated cultures were predominantly at the schizont stage or have already produced new daughter parasites resulting in increased overall parasitemia, CPP-MO treated parasites were blocked at all stages of intraerythrocytic development with fewer new daughter produced and the total parasitemia did not significantly increase. By 48 h post-invasion, untreated parasites reached 16% parasitemia with virtually all parasites at the ring stage, whereas the total parasitemia of cultures treated with the CPP-MO conjugate was half that of untreated cultures. From the 3% starting population of ring stage parasites, half remained at the schizont stages (FIG. 4A).

When the conjugate was added at the trophozoite (24 h) or early schizont (32 h) stages, the number of new daughter ring stage parasites produced was much more reduced compared to early treatment (FIGS. 4A and 4B), consistent with increased expression of PfGyrA during the trophozoite and schizont stages (Guerrier-Takada, et al., *Methods Enzymol* 313:442-456 (2000)). When these parasites were examined 56 h post-invasion up to 30% of the original population remained at the schizonts. Parasite cultures treated at 40 h post-invasion (2% schizonts and 2.5% rings) and analyzed 8 hours later produced 8% rings and contained the same number of schizonts, whereas untreated cultures were made exclusively of ring stage parasites (16% parasitemia). Examination of these parasites 16 h post-treatment, showed that the number of schizonts has decreased whereas the number of new daughter parasites produced did not increase, suggesting that the merozoites were either inviable or did not invade new red blood cells. In comparison, control cultures moved from 2% schizonts at 40 h postinvasion to 16% rings 56 h post-invasion.

Figure 4C:
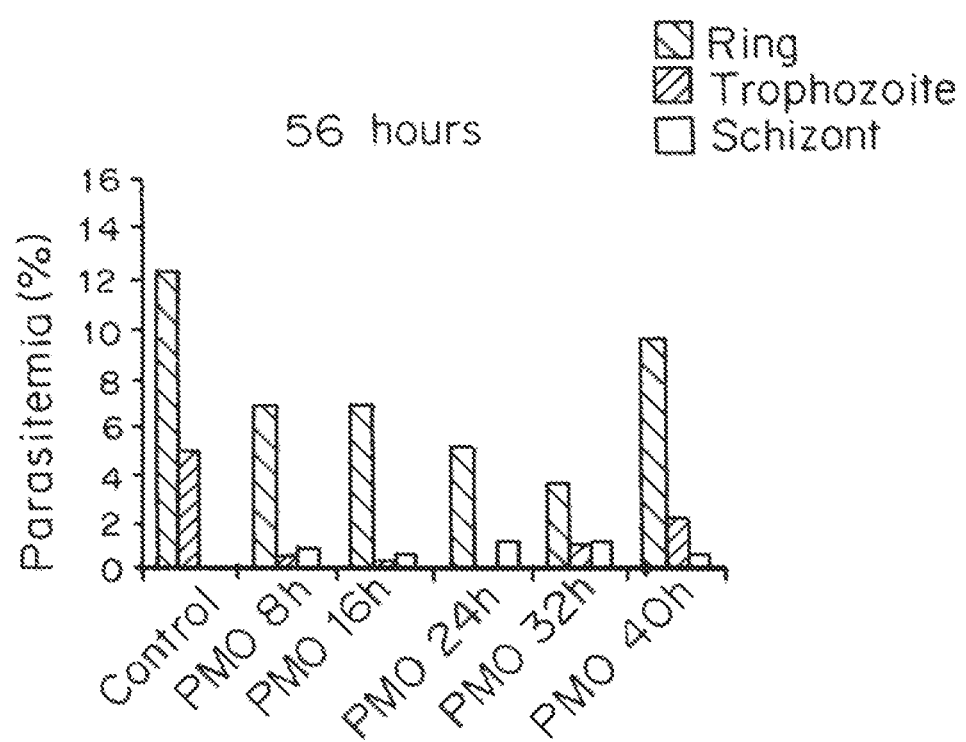
FIG. 4C is a bar graph showing the percentage (parasitemia (%)) of each parasite developmental stage (Ring, Trophozoite, Schizont) 56 hrs after merozoite invasion for control, or 2 μM of the CPP-MO treatment for 8 hr, 16 hr, 24 hr, and 32 hr time points.

The morphology of parasites following treatment with the conjugates at its $IC_{50}$ value were also determined. The majority of trophozoites and schizonts observed in treated cultures showed abnormal morphology (FIG. 4C).

Example 9

Pfgyra Specific PMO is Effective Against Both Drug-Sensitive and Drug-Resistant Strains Results Two CPP-MO conjugates were examined against drug-resistant isolates of *P. falciparum* (Table 3), one pyrimethamine resistant strain Hb3 and two chloroquine resistant strains W2 and Dd2. As shown in Table 3, both conjugates were equally effective against drug-sensitive and drug-resistant strains. The 3D7 strain was sensitive to all drugs, HB3 strain was resistant to pyrimethamine and Dd2 and W2 strains were resistant to chloroquine.

TABLE 12

Efficiency of two CPP-MO conjugates against chloroquine and pyrimethamine sensitive or resistant strains

| | % of inhibition | | | |
|---|---|---|---|---|
| | 3D7 | Hb3 | Dd2 | W2 |
| Plfgyr EGS | 95.9 ± 0.6 | 100 | 100 | 100 |
| Plfgyr2 EGS | 63.1 ± 0.4 | 73.0 ± 2.8 | 77.2 ± 0.5 | 75.3 ± 1.5 |

TABLE 12-continued

Efficiency of two CPP-MO conjugates against chloroquine
and pyrimethamine sensitive or resistant strains

| | % of inhibition | | | |
|---|---|---|---|---|
| | 3D7 | Hb3 | Dd2 | W2 |
| PYR 50 nM | 71.5 ± 0.05 | 0 | 0 | 8.6 ± 2.3 |
| CQ 25 nM | 99.0 ± 0.83 | 100 | 0 | 12.3 ± 2.3 |
| ART 25 nM | 91.5 ± 4.8 | 99.5 ± 0.2 | 18.8 ± 2.7 | 98.9 ± 0.6 |
| AQ 25 nM | 100 ± 0.0 | 100 | 97.8 ± 0.5 | 97.1 ± 0.4 |

Growth inhibition was determined using a SYBR Green I assay after culturing parasites for 3 days at 37° C. in the presence of the CPP-MOs or antimalarials. Results are mean of triplicate experiments±SD. The concentration of CPP-MO was 2 μM.

With the widespread of resistance to chloroquine and recent reports of resistance to artemisinin in southeast Asia (Anonymous, World Malaria Report. (World Health Organization) (2010)), efforts to develop new antimalarial therapies that utilize chemical classes that have not previously been used is urgent. The finding that specific PfGyrA conjugates are equally potent against drug sensitive and resistant strains, and the unique specific features of the PMO approach in targeting specific mRNA suggest that this strategy may find a wider use not only as a tool for functional analysis of *P. falciparum* genes but also as a selective therapeutic approach. The reliability of any new anti-malarial therapy is an important feature of its development. More than three mutation steps are needed to inactivate the conjugate providing the base changes in the morpholino oligonucleotide are not next to each other. In the unfortunate case where the mutations are contiguous, another part of the mRNA to be attacked can simply be chosen as the target. This has already been achieved in vitro with a second site in the PfgyrA mRNA.

We claim:

1. A composition comprising
   a basic cell penetrating peptide (CPP) comprising the amino acid sequence of SEQ ID NO:1 or a variant of SEQ ID NO:1 having at least 90% sequence identity to SEQ ID NO:1,
   and an external guide sequence (EGS).

2. The composition of claim 1 wherein the EGS is conjugated to the CPP.

3. The composition of claim 2 wherein the EGS is covalently conjugated to the CPP.

4. The composition of claim 1 wherein the EGS comprises a sequence antisense to a target mRNA.

5. The composition of claim 4 wherein the target mRNA is encoded by an essential microbial gene or antimicrobial resistance gene.

6. The composition of claim 4 wherein the target mRNA is encoded by a gene comprising the nucleic acid sequence SEQ ID NO: 4, 5, 6, 7, 8, 9, 12, 15, 16, 17, 18, or 19.

7. The composition of claim 1 wherein the EGS comprises the nucleic acid sequence SEQ ID NO: 14, 20, 21, 22, 23, 24, 25, 26, 27, 28, 29, 30, 31, 32, 33, 34, 35, 36, or 37.

8. The composition of claim 1 wherein the EGS is a morpholino oligonucleotide.

9. The composition of claim 1 wherein the composition further comprises an antimicrobial drug.

10. The composition of claim 1 wherein the CPP is not a fusion partner in a fusion protein.

11. The composition of claim 1 wherein the CPP comprises the amino acid sequence of SEQ ID NO: 1, 2, 3, 49, 50, 51, 52, or 53.

12. The composition of claim 1, wherein the CPP is conjugated to the EGS, and wherein the EGS comprises a sequence comprising five nucleotides of complementarity to an mRNA encoding an essential microbial gene or antimicrobial resistance gene.

13. The composition of claim 12, wherein the CPP-EGS conjugate binds more tightly to the mRNA relative to an unconjugated EGS having the same sequence.

14. The composition of claim 12, wherein the CPP comprises the amino acid sequence of SEQ ID NO:1.

* * * * *

UNITED STATES PATENT AND TRADEMARK OFFICE
CERTIFICATE OF CORRECTION

PATENT NO. : 9,801,948 B2
APPLICATION NO. : 14/343809
DATED : October 31, 2017
INVENTOR(S) : Sidney Altman, Alfred Bothwell and Choukri Mamoum It is certified that error appears in the above-identified patent and that said Letters Patent is hereby corrected as shown below:

In the Specification

Column 1, Lines 18-23, replace "This invention was made with government support under Agreement Nos, AI51507 awarded by the National Institute of Allergy and Infectious Diseases, R33 CA118631, R01 GM065835, and AI041927 awarded by the National Institutes of Health. The government has certain rights in the invention." with "This invention was made with government support under CA118631, AI041927, GM065835 and DK051507 awarded by National Institutes of Health. The government has certain rights in the invention."

Signed and Sealed this
Twenty-third Day of June, 2020

Andrei Iancu
*Director of the United States Patent and Trademark Office*